United States Patent
Tusé et al.

(12) 
(10) Patent No.: US 6,482,799 B1
(45) Date of Patent: Nov. 19, 2002

(54) SELF-PRESERVING MULTIPURPOSE OPHTHALMIC SOLUTIONS INCORPORATING A POLYPEPTIDE ANTIMICROBIAL

(75) Inventors: Daniel Tusé, Menlo Park, CA (US); Kristien Mortelmans, Los Altos Hills, CA (US); Leslie A. Hokama, Los Altos, CA (US); Michael E. Selsted, Irvine, CA (US); Larry L. Chapoy, Barrington, IL (US); Michael H. Quinn, Valparaiso, IN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/318,195

(22) Filed: May 25, 1999

(51) Int. Cl.⁷ .................................. A61K 38/00
(52) U.S. Cl. ..................... 514/14; 514/15; 424/405; 422/28; 530/327; 530/328
(58) Field of Search ................. 514/14, 15; 424/405; 422/28; 530/327, 328

(56) References Cited

U.S. PATENT DOCUMENTS

| | | | |
|---|---|---|---|
| 5,141,665 A | | 8/1992 | Sherman |
| 5,547,939 A | | 8/1996 | Selsted |
| 5,549,894 A | | 8/1996 | Hunt |
| 5,696,171 A | | 12/1997 | Rupp et al. |
| 6,037,328 A | * | 3/2000 | Hu et al. ............... 514/23 |
| 6,162,393 A | * | 12/2000 | De Bruiju et al. .......... 422/28 |

FOREIGN PATENT DOCUMENTS

| | | |
|---|---|---|
| EP | 0 095 524 A1 | 12/1983 |
| EP | 0 766 970 A2 | 4/1997 |
| WO | WO 96/25183 | 8/1996 |
| WO | WO 97/29765 | 8/1997 |

OTHER PUBLICATIONS

Cullor et al, "In vitro antimicrobial activity of defensins against ocular pathogens," *Arch. Ophthalmol.* (1990) 108: 861–864.

Maloy and Kari, "Structure–activity studies on magainins and other host defense peptides," *Biopolymers* (1995) 37: 105–122.

Sousa et al., "The use of synthetic cecropin ($D_5C$) in disinfecting contact lens solutions," *Clao J.* (1996) 22(2): 114–117.

* cited by examiner

*Primary Examiner*—Dwyane C. Jones
*Assistant Examiner*—C. Delacroix-Muirheid
(74) *Attorney, Agent, or Firm*—Townsend and Townsned and Crew LLP

(57) ABSTRACT

This invention provides a novel anti-microbial system suitable for formulation in a wide variety of ophthalmic solutions. In particular the composition comprises an antimicrobial peptide that is an indolicidin and a buffer compatible with application to a mammalian eye, wherein the buffer is a Good's buffer or the buffer has a halide ion concentration less than 0.85 wt %. The compositions are useful for storing, cleaning, or disinfecting a contact lens. In particular the compositions are self-preserving upon lengthy storage, effective in cleaning and sterilizing contact lenses upon exposure of the lens to the composition, do not require the need for physical or thermal treatment of the lens and enable the immediate application of the lens to the eye without the need for neutralization, deactivation or washing.

59 Claims, 6 Drawing Sheets

SEQUENCE LISTING

```
<160> NUMBER OF SEQ ID NOS: 15

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:indolicidin
      (naturally occurring), Indol-12-R13-R-NH-2
<221> NAME/KEY: MOD_RES
<222> LOCATION: (13)
<223> OTHER INFORMATION: Xaa = argininamide

<400> SEQUENCE: 1

Ile Leu Pro Trp Lys Trp Pro Trp Trp Pro Trp Arg Xaa
 1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:indolicidin
      analog Indol-12-R13-R-OH

<400> SEQUENCE: 2

Ile Leu Pro Trp Lys Trp Pro Trp Trp Pro Trp Arg Arg
 1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence:indolicidin
      analog Indol-12-R13-N-NH-2
<221> NAME/KEY: MOD_RES
<222> LOCATION: (13)
<223> OTHER INFORMATION: Xaa = asparaginamide

<400> SEQUENCE: 3

Ile Leu Pro Trp Lys Trp Pro Trp Trp Pro Trp Arg Xaa
 1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:indolicidin
      analog Indol-12-K13-K-NH-2
<221> NAME/KEY: MOD_RES
<222> LOCATION: (13)
<223> OTHER INFORMATION: Xaa = lysinamide
```

```
<400> SEQUENCE: 4

Ile Leu Pro Trp Lys Trp Pro Trp Trp Pro Trp Lys Xaa
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:indolicidin
      analog Indol-12-K-NH-2
<221> NAME/KEY: MOD_RES
<222> LOCATION: (12)
<223> OTHER INFORMATION: Xaa = lysinamide

<400> SEQUENCE: 5

Ile Leu Pro Trp Lys Trp Pro Trp Trp Pro Trp Xaa
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:indolicidin
      analog Indol-12-R-OH

<400> SEQUENCE: 6

Ile Leu Pro Trp Lys Trp Pro Trp Trp Pro Trp Arg
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:indolicidin
      analog Indol-12-R13-K-NH-2
<221> NAME/KEY: MOD_RES
<222> LOCATION: (13)
<223> OTHER INFORMATION: Xaa = lysinamide

<400> SEQUENCE: 7

Ile Leu Pro Trp Lys Trp Pro Trp Trp Pro Trp Arg Xaa
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:indolicidin
      analog
<221> NAME/KEY: MOD_RES
<222> LOCATION: (9)
<223> OTHER INFORMATION: Xaa = tryptophanamide

<400> SEQUENCE: 8

Ile Leu Pro Trp Lys Trp Pro Trp Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:indolicidin
      analog
```

```
<400> SEQUENCE: 9

Ile Leu Pro Trp Lys Trp Pro Trp Trp
 1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:indolicidin
      analog
<221> NAME/KEY: MOD_RES
<222> LOCATION: (12)
<223> OTHER INFORMATION: Xaa = argininamide

<400> SEQUENCE: 10

Leu Pro Trp Lys Trp Pro Trp Trp Pro Trp Arg Xaa
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:indolicidin
      analog
<221> NAME/KEY: MOD_RES
<222> LOCATION: (11)
<223> OTHER INFORMATION: Xaa = argininamide

<400> SEQUENCE: 11

Pro Trp Lys Trp Pro Trp Trp Pro Trp Arg Xaa
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:indolicidin
      analog
<221> NAME/KEY: MOD_RES
<222> LOCATION: (10)
<223> OTHER INFORMATION: Xaa = argininamide

<400> SEQUENCE: 12

Trp Lys Trp Pro Trp Trp Pro Trp Arg Xaa
 1               5                  10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:indolicidin
      analog
<221> NAME/KEY: MOD_RES
<222> LOCATION: (9)
<223> OTHER INFORMATION: Xaa = argininamide

<400> SEQUENCE: 13

Lys Trp Pro Trp Trp Pro Trp Arg Xaa
 1               5

<210> SEQ ID NO 14
<211> LENGTH: 12
<212> TYPE: PRT
<213> ORGANISM: Artificial Sequence
<220> FEATURE:
```

```
<223> OTHER INFORMATION: Description of Artificial Sequence:indolicidin
      general structure
<221> NAME/KEY: MOD_RES
<222> LOCATION: (12)
<223> OTHER INFORMATION: Xaa = any amino acid

<400> SEQUENCE: 14

Ile Leu Pro Trp Lys Trp Pro Trp Trp Pro Trp Xaa
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:indolicidin
      general structure
<221> NAME/KEY: MOD_RES
<222> LOCATION: (12)..(13)
<223> OTHER INFORMATION: Xaa = any amino acid

<400> SEQUENCE: 15

Ile Leu Pro Trp Lys Trp Pro Trp Trp Pro Trp Xaa Xaa
 1               5                  10
```

SELF-PRESERVING MULTIPURPOSE OPHTHALMIC SOLUTIONS INCORPORATING A POLYPEPTIDE ANTIMICROBIAL

CROSS-REFERENCE TO RELATED APPLICATIONS

[NOT APPLICABLE]

STATEMENT AS TO RIGHTS TO INVENTIONS MADE UNDER FEDERALLY SPONSORED RESEARCH AND DEVELOPMENT

[NOT APPLICABLE]

FIELD OF THE INVENTION

This invention relates to novel ophthalmic compositions useful for conditioning and/or cleaning and/or disinfecting contact lenses. In particular, the present invention provides ophthalmic compositions that contain one or more indolicidin antimicrobial polypeptides and typically have a low halide ion concentration.

BACKGROUND OF THE INVENTION

During normal use, contact lenses are "soiled" or "contaminated" with a wide variety of compounds that immediately or ultimately degrade lens performance. For example, while being worn on the eye, a contact lens is liable to be contaminated with biological materials such as protein or lipid that are found in the tear fluid and that adheres to the surfaces of the contact lens. In handling or cleaning the contact lens, sebum (skin oil) or cosmetics or other materials adhering to the hands of the user tend to soil the contact lens. In addition, particularly as contact lenses accumulate organic contaminants they promote the growth on their surface of a wide range of microbes.

If the contact lens is worn on the eye with such contaminants on its surface, the contact lens suffers from deteriorated water wettability or hydrophilicity and lowered oxygen permeability, causing considerable discomfort to the lens wearer. In addition, the lens wearer may suffer from deterioration in his eyesight, pain in the eye, hyperemia or congestion of the eye, due to the continuous wearing of the contaminated contact lens. In addition, a contaminated lens can become immunogenic stimulating an adverse immune response on the eye and associated tissues. In view of this, it is important to remove the soil debris adhering to the contact lens surfaces and to disinfect the lens for safe and comfortable wearing of the contact lens on the user's eye.

In view of these, and other, factors effecting lens performance, a care regimen for contact lenses typically involves various functions, such as regularly cleaning the lens with a contact lens solution. Rinsing of the contact lens is generally required following cleaning to remove loosened debris and to remove potential irritants in the cleaning solution. Additionally, the regimen may include treatment to disinfect the lens, treatment to render the lens surface more wettable prior to insertion in the eye, or treatment to condition (e.g., lubricate or cushion) the lens surface so that the lens is more comfortable in the eye. As a further example, a contact lens wearer may need to rewet the lens during wear by administering directly in the eye a solution commonly referred to as rewetting drops.

Separate solutions may be provided for the individual segments of the care regimen. For convenience purposes, multipurpose contact lens solutions have gained popularity, i.e., solutions which can be used for several segments of the care regimen.

As an example, multipurpose contact lens solutions that can be used for cleaning, storage and conditioning of contact lenses have been suggested (see, e.g., U.S. Pat. No. 5,141,665 (Sherman) discloses a cleaning, conditioning, storing and wetting system for rigid gas permeable contact lenses. The system is described as including: (1) a cleaning, conditioning and storing solution; and (2) a separate wetting solution, where both solutions include a disinfectant or preservative. Lenses treated with the first solution are rinsed and then wet with the separate wetting solution prior to insertion in the eye.

Multipurpose contact lens solutions that effectively clean a contact lens, and can also be used to treat the lens immediately prior to insertion of the lens in the eye, are much more challenging multipurpose solutions to develop. Conventional surface active agents having good cleaning activity for contact lens deposits, as well as various other components such as antimicrobial agents included as a preservative or disinfectant, tend to be irritating to the eye. Accordingly, new ophthalmic compositions, particularly multipurpose formulations, are desirable.

In recent years, researchers have come to recognize that many organisms use peptides as part of their host defense systems. These organism include a full range of species from prokaryotes to humans. The antimicrobial peptides can be subdivided into a number of groups based on their amino acid content, structure and source. Several reviews of several classes of these peptides have been recently published (See, for example, Lehrer & Ganz (1966) *Annal. N.Y. Acad. Sci.*, 797:228–239; Maloy & Kari (1995) *Biopolymers*, 37:105–122).

Antimicrobial peptides have common structural features, including a net cationic charge due to the presence of multiple charged residues (Arg, Lys), the presence of multiple cysteine residues, and in most cases the ability to form amphipathic structures. These properties are important for the mechanism of action that is currently thought to involve a non-receptor-mediated interaction with the anionic phospholipid bilayer of the target cell, followed by incorporation of the peptide into the membrane, and a resulting disruption of the membrane structure.

The spectrum of activity of host defense peptides is very broad, killing many species of bacteria, protozoa, fungi, and virally infected cells and even cancer cells (Maloy & Kari (1995) *Biopolymers*, 37:105–122). Moreover, these peptides have a low toxicity on most healthy mammalian cells and tissues. It is thought that the peptides are preferentially selective for prokaryotic membranes because of the lipid composition of the membrane. In particular, there is a higher concentration of anionic phospholipids in the outer leaflet of bacteria than in normal eukaryotic membranes, and cholesterol is present in mammalian membranes but not in bacterial membranes. Whatever the reason for the preference, the selectivity of antimicrobial peptide for prokaryotes compared to eukaryotes, these peptides are ideal components in products intended for human use.

While attempts have been made to utilize antimicrobial polypeptides in ophthalmic solutions, to date such efforts have been largely unsuccessful. For example, Sousa et al. (1996) *CLAO J.*, 22(2):114–117, showed that the use of a synthetic cecropin analog in combination with various ophthalmic solutions failed to be highly effective in disinfecting, particularly when used by itself. Cullor et al. (1990) *Arch.*

Ophthalmol., 108: 861–864 examined the in vitro efficacy of rabbit defensins, NP-1 and NP-5, against ocular pathogens isolated from cases of severe ulcerative keratitis in humans and horses. Unfortunately, these antimicrobial peptide-containing compositions were found to have toxicity to human eye tissue. Similarly U.S. Pat. No. 5,549,894 describes ophthalmic compositions containing D-enantiomeric peptides, such as cecropins, magainins and defensins. These polypeptides, however are toxic and eye care products containing these peptides can not be made in commercial quantities, as the peptides must be chemically synthesized and can not be made using biological expression systems.

SUMMARY OF THE INVENTION

This invention provides novel ophthalmic solutions based on the use of indolicidins as antimicrobial agents. In particular, the solutions of this invention are self-preserving and require no additional preservatives or disinfectants. The solutions are well suited for ophthalmic use and are effective in cleaning, disinfecting, and sterilizing the contact lens upon exposure to the composition without the need for physical or thermal treatment of the lens. Moreover, because indolicidins are safe for topical application to the eye, the solutions enable immediate application of the contact lens to the eye without the need for neutralization, deactivation, or washing any of the compositions' components. In addition, the compositions have extremely long shelf life at room temperature.

In particular, it was a discovery of this invention that indolicidins are inactivated by the presence of chloride in typical buffer systems (e.g., phosphate buffered saline (PBS)), but can act as highly effective antimicrobial compounds when formulated either in solutions containing a low concentration of halide ion, or when formulated in a Good's buffer (e.g., Tris(hydroxymethyl)aminomethane (TRIS).

Embodiments of the invention include an ophthalmic composition for storing, cleaning, or disinfecting a contact lens, the composition comprising an indolicidin in an antimicrobially effective amount and a buffer compatible with application to a mammalian eye, wherein the buffer has a halide ion concentration of less than 0.85%. The composition may additionally comprise boric acid or a borate salt present in a microbistatic amount, a poloxamer, a chelating agent, or a divalent cation.

In a preferred embodiment, the composition comprises indolicidin, wherein the indolicidin is present in a concentration ranging from 2 µg/ml to 100 µg/ml; and a buffer comprising a sodium phosphate or potassium phosphate in a concentration ranging from about 1 mM to about 10 mM; a boric acid or borate salt in a concentration ranging from about 0.1% to about 5%; a poly(oxyethylene)-poly(oxypropylene) block copolymer in a concentration ranging from about 0.25 to about 0.5%; a chelator in a concentration ranging from about 0.01% and about 0.5%; and a divalent cation in a concentration ranging from about 5 mM to about 50 mM.

An alternative composition of the invention for storing, cleaning, or disinfecting a contact lens comprises an indolicidin and a Good's buffer. The composition may additionally comprise boric acid or a borate salt present in a microbistatic amount, a surfactant (preferably a poloxamer), a chelating agent, or a divalent cation.

In additional embodiments, the invention comprises a multipurpose solution for the care of a contact lens, the solution comprising indolicidin and a buffer wherein the solution is suitable for two or more actions, including contact lens disinfection, contact lens storage, contact lens cleaning, contact lens conditioning and rehydrating, contact lens moistening, and contact lens lubricating. The solution comprises indolicidin and a buffer compatible with application to a mammalian eye wherein the halide ion concentration of the buffer is less than 0.85%. Alternatively, the solution may comprise indolicidin and a Good's buffer. Such a multipurpose solution may additionally comprise a demulcent and a poloxamer.

The invention includes a method of disinfecting a contact lens, the method comprising contacting the contact lens with a composition of the invention. Further, a contact lens storage system is included in the invention, which comprises a container containing an opthalmic composition of the invention.

Alternatively, the invention may comprise a method of packaging a contact lens, the method comprising sealing a contact lens in a container with an ophthalmic composition of the invention or a method of disinfecting a contact lens storage vessel comprising contacting the storage vessel with a composition of the invention.

Definitions

The term Good's buffer refers to a buffer of the type described by Good et al. (1966) *Biochem.*, 5: 467–477. Preferred Good's buffers include tris(hydroxymethyl) aminomethane (TRIS), N-(2-acetamido)iminodiacetic acid (ADA), piperazine-1,4-bis(2-ethanesulfonic acid) (PIPES), N-(2-acetamido)-2-aminoethanesulfonic acid (ACES), N,N-bis(2-hydroxyethyl)-2-aminoethanesulfonic acid (BES), 3-morpholinopropanesulfonic acid (MOPS), N-tris (hydroxymethyl) methyl-2-aminoethanesulfonic acid (TES), 2,4-(2-hydroxyethyl)-1-piperazinyl ethanesulfonic acid (HEPES), 3,4-(2-hydroxyethyl)-1-piperazinyl propanesulfonic acid (EPPS), N-tris(hydroxymethyl) methylglycine (Tricine), N,N-bis (2-hydroxyethyl)glycine (Bicine), N-cyclohexyl-2-aminoethanesulfonic acid (CHES), and N-cyclohexyl-3-aminopropanesulfonic acid (CAPS), with TRIS being most preferred.

The term "antimicrobial" is used herein to refer to the ability of a compound, i.e. an indolicidin, to decrease the population of microscopic flora and/or fauna on a surface, e.g., on a contact lens surface. Antimicrobial activity includes bacteriostatic or antibacterial activity, antifungal activity, antialgal activity, and the like. An antimicrobial need not eliminate all microbes, but simply decreases the viable population on the treated surface.

Similarly, "antimicrobial activity" refers to the ability of a compound to inhibit or irreversibly prevent the growth of a microorganism. Such inhibition or prevention can be through a microbicidal action or microbistatic inhibition.

"Microbicidal inhibition" as used herein refers to the ability of the antimicrobial to kill or irrevocably damage the target organism.

"Microbistatic inhibition" as used herein refers to the ability of the microbistatic or antimicrobial compound to inhibit or to retard the growth of the target organism without causing death. Microbicidal or microbistatic inhibition can be applied to either an environment either presently exhibiting microbial growth (i.e., therapeutic treatment) or an environment at risk of supporting such growth (i.e., prevention or prophylaxis).

"Broad spectrum antimicrobial activity" refers to the ability of a compound to inhibit or prevent the survival or growth of various prokaryotic and eukaryotic microorganisms including, for example, protozoans such as *Giardia lamblia,* fungi such as Cryptococcus, various genera of bacteria such as Escherichia, Salmonella and Staphylococcus, and enveloped viruses. Antimicrobial activity can occur through a microbicidal or a microbistatic inhibition.

"Microbicidal inhibition" refers to the ability of a compound to reduce or inhibit the survival of a microorganism by killing or irreversibly damaging it, whereas the term "microbistatic inhibition" refers to the ability of a compound to inhibit the growth of a target microorganism without killing it. A compound having microbicidal or microbistatic inhibition can be applied to an environment that presently allows for the survival or growth of a microorganism (i.e., therapeutic treatment) or to an environment at risk of supporting such survival or growth (i.e., prevention or prophylaxis).

"Antimicrobial selectivity" refers to the relative amount of antimicrobial activity of an analog as compared to its cytolytic activity against normal cells in a subject.

The term "ophthalmic solution" refers to a solution that forms a stock solution for the preparation of solutions for the packaging, shipping, storage, cleaning, maintenance, use, or rehydration of contact lenses or is useful itself for one or more of these purposes.

As used herein, the terms "ophthalmically acceptable composition" or "compatible with application to an eye" means a composition which can be placed into a human eye without causing any substantial discomfort, damage, or harm.

The terms "stable" or "stability" when used with respect to an indolicidin refer to the retention of antimicrobial activity (e.g., as measured by a minimal inhibitory concentration (MIC) assay, see, e.g., Example 10). When the indolicidin or indolicidin-based formulation is unstable, it looses activity with time. The indolicidin or indolicidin-based composition is deemed unstable over a selected period time under particular storage conditions (e.g., at room temperature in a particular type of receptacle), when the indolicidin or indolicidin-based composition shows a significant diminution in microbicidal activity against one or more selected test organisms (e.g., Pseudomonas, sp.). A significant diminution is typically at least a two percent diminution, preferably at least a 5 percent diminution, more preferably at least a 10% diminution and most preferably at least a 20% diminution in activity. Conversely, the indolicidin or indolicidin-based composition is said to be stable over the particular time period/storage conditions, when there is less than a 20%, preferably less than a 10%, more preferably less than a 5%, and most preferably less than a 2% or 1% decrease in activity as determined by a MIC assay.

The term "weight percent" or "wt %" as used herein refers to the number of grams of material per 100 ml of solution.

The term "lens disinfection" refers to a reduction or elimination of microbial organisms present on a contact lens.

The term "lens storage", refers either to the short term storage e.g., on the order of hours, days or weeks, by a user, e.g, when not wearing the lens, or long term storage, e.g., on the order of days, weeks, months, or years, as in the storage prior to sale or first use of the lens.

"Lens cleaning" refers to a reduction and/or elimination of contaminants on the surface of a contact lens. Such contaminants include, but are not limited to lipids, fats, oils, proteins, or microbial organisms.

"Lens conditioning and/or rehydrating" refers to the addition of water to a lens, e.g., a soft contact lens thereby increasing the water content of the lens.

"Lens lubricating" refers to the addition of water, surfactants, or demulcents to decrease the coefficient of friction between a lens and the surface of an eye. Such lubricating can be by treatment of the lens prior to or after insertion into the eye.

The term "mammalian eye" is used to refer the to eye of any animal in the order mammalia. Such animals include, but are not limited to horses, cats, dogs, rabbits, mice, goats, sheep, non-human primates and humans. Thus, the solutions are contemplated for use in veterinary applications as well as human use. In preferred embodiments, the mammalian eye is a "healthy" eye. However, under certain circumstances, the eye may be unhealthy, e.g., infected, inflamed, or otherwise irritated.

The terms "polypeptide", "peptide", or "protein" are used interchangeably herein to designate a linear series of amino acid residues connected one to the other by peptide bonds between the alpha-amino and carboxy groups of adjacent residues.

"Amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway.

Indolicidin (SEQ ID NO: 1) is a thirteen amino acid polypeptide that has a high tryptophan content, exhibits broad spectrum antimicrobial activity and has antimicrobial selectivity. As used herein, indolicidins should be understood to include both native indolicidin and analogs thereof. Indolicidins and their use in antimicrobial formulations are described in U.S. Pat. No. 5,547,939. Indolicidins useful in accordance with the present invention have similar tryptophan content, antimicrobial activity and antimicrobial selectivity to native indolicidin (see Table 2). In general, indolicidins useful in accordance with the present invention have the general structure $H_2N$-I-L-P-W-K-W-P-W-W-P-W-X (SEQ ID NOS:14 and 15), where X designates one or two independently selected amino acids. Indolicidins typically contain twelve or thirteen amino acids (although the indolicidins of this invention can range in length up to about 45 amino acids) and are tryptophan-rich. Indolicidin, for example, has a tryptophan content of about 38 percent (5/13 residues). Indolicidins are further characterized by having substantially the same sequence as naturally occurring indolicidin. As used herein, the term "substantially the same sequence" means that the peptide sequence of an indolicidin analog has at least 60%, preferably 70%, more preferably 80%, and most preferably 90%, 95%, or 98% sequence identity with the sequence of indolicidin (SEQ ID NO: 1). Thus, a limited number of modifications can be made to the indolicidin peptide sequence to obtain indolicidins that have a desirable antimicrobial selectivity such as increased antimicrobial activity or decreased hemolytic activity as compared to naturally occurring indolicidin. For example, an indolicidin analog can have the same peptide sequence as indolicidin but can be modified, for example, by containing a C-terminal reactive group other than an amide, which is found in naturally occurring indolicidin (see, for example, (SEQ ID NO: 5).

"Tryptophan-rich peptide" means a peptide having at least about 25% of its residues consisting of tryptophan.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351–360. The method used is similar to the method described by Higgins & Sharp (1989) CABIOS 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul (1993) Proc. Natl. Acad. Sci. USA, 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions.

The term "conservative substitution" is used in reference to proteins or peptides to reflect amino acid substitutions that do not substantially alter the activity (e.g., antimicrobial activity) of the molecule. Typically conservative amino acid substitutions involve substitution one amino acid for another amino acid with similar chemical properties (e.g., charge or hydrophobicity). The following six groups each contain amino acids that are typical conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K)
5) Isoleucine (I), Leucine (L), Methionine (M), Valine (V); and
6) Phenylalanine (F), Tyrosine (Y), Tryptophan (W)

DETAILED DESCRIPTION

I. Indolicidin-based Ophthalmic Solutions

Figure 1:
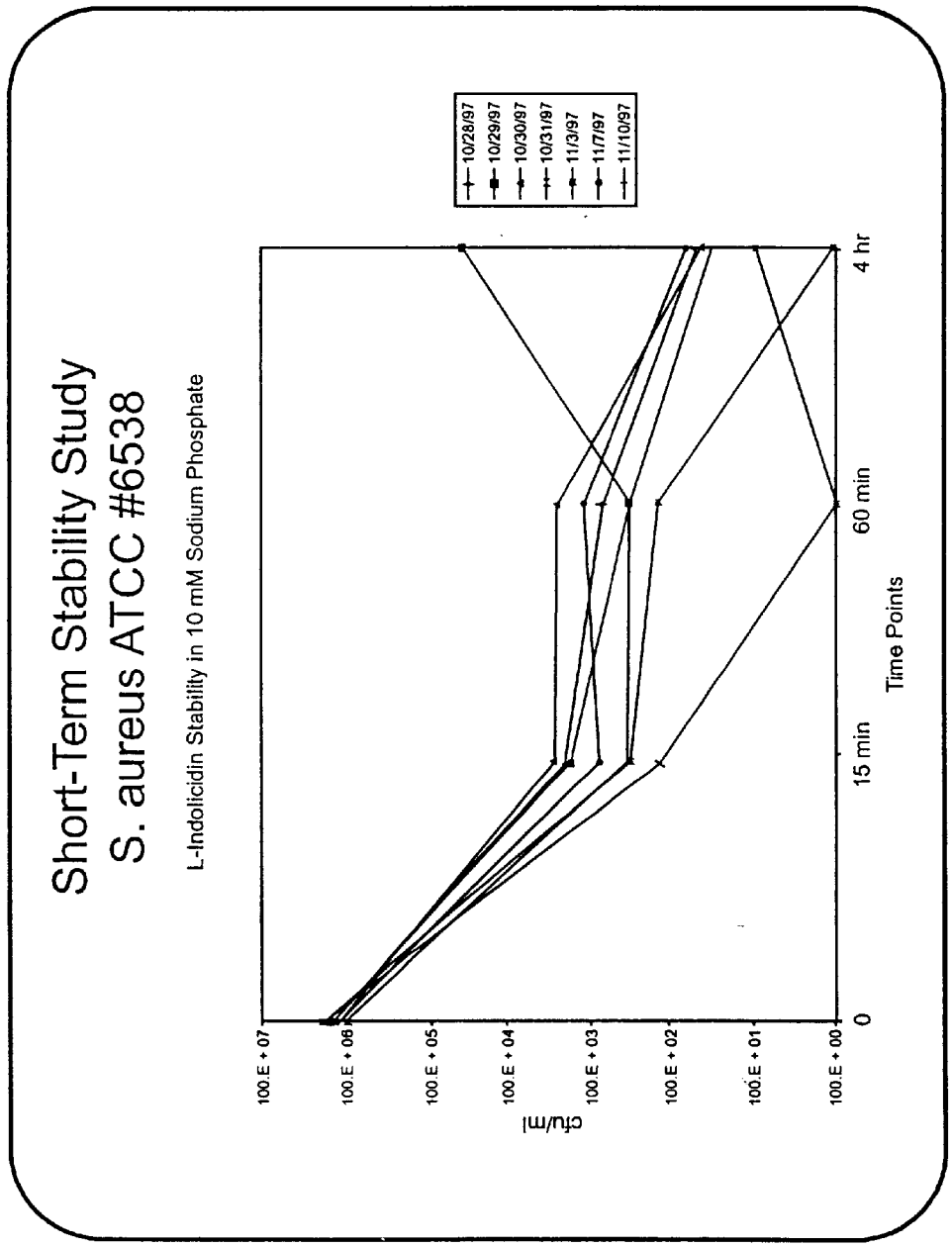
FIG. 1 illustrates the short term stability of unfrozen L-indolicidin in 10 mM sodium phosphate buffer as measured against S. aureus. The solution was stable exhibiting a time-dependent kill with a 4-log kill after a 4 hour exposure.

This invention provides novel compositions for the packaging, routine care, and use of contact lenses. Contact lens maintenance and use requires a number of activities including, but not limited to, cleaning and rinsing of the lens, disinfection of the lens, rewetting (e.g., rehydrating and/or rendering the lens more wettable prior to insertion in the eye), conditioning the lens (e.g., treatment to lubricate and/or cushion the lens surface), and the like. While separate "ophthalmic" solutions can be used for one or more of these activities, for convenience purposes, multipurpose contact lens solutions (i.e., solutions which can be used for several segments of the care regimen) have gained popularity.

Regardless of whether a single purpose or multi-purpose solution is used, to minimize the risk of infection (e.g., of the cornea or inner eye lid), it is preferable to maintain the care solutions and the contact lens in as sterile a condition as possible. To this end, various antimicrobial agents have been incorporated into various solution systems. Such agents, include, but are not limited to, peroxide, thimerosol, polyquaternium-1, and the like. Use of these antimicrobial agents, is ultimately limited, particularly in multipurpose solutions because, particularly over a prolonged period, they tend to irritate and inflame the eye and adjacent tissues.

It was a discovery of this invention that antimicrobial polypeptides can be used to advantage as disinfectants (antimicrobials) in a wide variety of single-purpose and multipurpose ophthalmic solutions. It was, however, a surprising discovery of this invention that the antimicrobial activity of indolicidins is reduced and in many cases eliminated, by physiologically relevant concentrations (e.g., about 90 mM to about 150 mM), or higher concentrations, of halide ions (e.g., $Cl^-$, $I^-$, $Fl^-$, and the like). Thus, in a preferred embodiment, this invention provides indolicidin-containing ophthalmic solutions having broad spectrum antimicrobial activity, comprising an indolicidin in a buffer compatible with application to a mammalian eye, where the buffer has a halide ion concentration less than 0.85 weight percent (wt %), preferably less than about 0.80 wt %, more preferably less than about 0.75 wt %, and most preferably less than about 0.5 wt %. In some embodiments the halide ion concentration is substantially or essentially zero.

It was also a surprising discovery of this invention that indolicidin activity was substantially less affected by halide ions when it is present in a Good's buffer (e.g., HEPES, TRIS, PIPES, etc.). However, solutions formulating these buffers are generally not broad-spectrum and tend to have antimicrobial activity against particular bacteria (or other agents) depending on the particular formulation. Thus, in another preferred embodiment, the ophthalmic solutions are "narrow-spectrum" solutions that comprise an indolicidin in a Good's buffer and these systems can optionally contain one or more species of halide ion.

When formulated in accordance with this invention, the indolicidin-containing solutions are powerful antimicrobial compositions comparable in efficacy to peroxide treatments of contact lenses. Unlike peroxides, however, the indolicidin treated lenses can be immediately inserted in the eye without rinsing or other neutralization of the solution. Moreover, the indolicidins do not appear to be either allergenic or immunogenic when used in this context.

Mechanical parameters of diameter consistency, base curve consistency, tensile strength, edge integrity, comfort, and handling characteristics can also be adequately maintained in a formulation of the indolocidin solution in accordance with the invention, along with the optical properties. In order to test these parameters, ANSI Z80.20 may be used as a standard for establishing finished lens parameters.

Having discovered that indolicidin activity retained in low halide ion or halide ion free (e.g., Cl-free) system, or in Good's buffer systems, indolicidins can be used in a wide variety of formulations and purposes as described below.

II. Indolicidin Formulations

Depending on intended use, the indolicidin containing ophthalmic solutions of this invention can be compounded with one or more agents to facilitate their use in a wide variety of contexts. Such agents include, but are not limited to surfactants/detergents, chelator cations (especially of divalent cations), osmotic stabilizers, bacteriostatic adjuvants (in addition to the indolicidins themselves), demulcents, viscosity-adjusting agents, and lubricants. In most preferred embodiments, the added reagents are selected for compatibility with administration to a mammalian eye and are thus selected to minimize discomfort or adverse physiological effects if accidentally or deliberately administered to the surface of a mammalian eye.

Preferred components that may comprise the ophthalmic solutions of this invention are illustrated in Table 1.

TABLE 1

Preferred constituents of indolicidin based ophthalmic solutions.

| Component | Function | Preferred Agents | Typical Range |
|---|---|---|---|
| indolicidin | microbicide | indolicidin and analogues | length ranging from about 9 to about 13 amino acids, concentration ranging from about 3.125 µg/ml to about 100 µg/ml, |
| buffer | Maintain pH and tonicity to stabilize indolicidin in active conformation. Prolong shelf life. | Sodium phosphate Good's Buffers (TRIS HEPES PIPES) | |
| surfactant/detergent* | facilitate cleaning | cationic anionic zwitterionic non-ionic (poloxamer, pluronic) | 0.01–3 wt % |
| cation chelator* | Increase activity of indolicidin. Improve shelf life. | EDTA EGTA EDBA | 0.01–0.2 wt % |
| osmotic stabilizer* (tonicity adjusting agent) | Maintain or adjust desired osmolarity (tonicity). | NaCl KCl mannitol sorbitol dextrose dextrin halide salt of monovalent cation | 0.1 to 1 wt % |
| divalent cation*+ | Improved antimicrobial activity against gram negative bacteria | $Mg^{2+}$ $Ca^{2+}$ $Ba^{2+}$ | |
| bacteriostatic adjuvant* | Reduce bacterial (microbial) contamination. Improve shelf life. | boric acid thimerosol | 0.01–2.5 wt % |
| demulcent* | Decrease eye irritation | cellulose derivatives, polyols, | |
| viscosity adjusting agent* | Thickener to slow evaporation, increase cushion, lubrication | glycerin | |

*Optionally present
+Omitted when chelator is present.

The various components listed as optional above, can be mixed and matched in different preferred formulations to optimize one or more activities of the indolicidin-based ophthalmic solution. Thus, for example, where the solution is intended to act solely as a bacteriocide, it might comprise only a buffer and one or more indolicidins, and optionally a bacteriostatic adjuvant and/or a divalent cation. In such an instance higher indolicidin concentrations may be utilized. Where the solution is to be used as a contact lens cleaning solution, the indolicidin/buffer formulation preferably also contains a surfactant, more preferably a poloxamer. Where the solution is used as an "eye-drop" or "conditioning solution for direct application to the eye, the indolicidin/ buffer formulation preferably includes a lubricant and/or viscosity adjusting agent and/or a demulcent. In addition, the solution can be formulated with substantially all of these agents (although it will be recognized that there is little to be gained by adding a chelator of divalent cations and the divalent cations themselves) as a multi-purpose solution for all of these, and other, uses.

A) Preferred Components of Indolicidin-based Ophthalmic Solutions

1) Indolicidins for use in ophthalmic solutions.

As indicated above, it was a surprising discovery of this invention that indolicidins can be used in the formulation of ophthalmic solutions for the care and use of contact lenses. Indolicidin (SEQ ID NO: 1) is a thirteen amino acid peptide that has a high tryptophan content, exhibits broad spectrum antimicrobial activity and has antimicrobial selectivity. Indolicidins (e.g., indolicidin and its analogues) are ideal for use in ophthalmic solutions because they have now been discovered to be safe to the eye, to not cross the intact cornea of animals, and to not lead to undue irritation upon repeated exposure. Furthermore, the indolicidins can act as a solution preservative because they are self-sterilizing. The broad spectrum antimicrobial activity of indolicidins along with their low immunogenicity and extremely long shelf life when stored in buffered formulations, even at room temperature, makes indolicidins an ideal antimicrobial agent for use in ophthalmic solutions.

As used herein, indolicidins should be understood to include both native indolicidin and analogs thereof. Indolicidins and their use in antimicrobial formulations are described in U.S. Pat. No. 5,547,939. Indolicidins useful in accordance with the present invention have similar tryptophan content, antimicrobial activity and antimicrobial selectivity to native indolicidin (see, e.g., Table 2, which sets forth preferred indolicidins).

TABLE 2

Sequence and molecular mass of indolicidin and indolicidin analogs

| Name | Amino Acid Sequence | Seq ID No: | Mol. Wt.* |
|---|---|---|---|
| Indol-$R^{12}R^{13}$-$NH_2$ | $H_2N$-ILPWKWPWWPWRR-$CONH_2$ | 1 | 1907 |
| Indol-$R^{12}R^{13}$-OH | $H_2N$-ILPWKWPWWPWRR-OH | 2 | 1908 |
| Indol-$R^{12}N^{13}$-$NH_2$ | $H_2N$-ILPWKWPWWPWRN-$CONH_2$ | 3 | 1937 |
| Indol-$K^{12}K^{13}$-$NH_2$ | $H_2N$-ILPWKWPWWPWKK-$CONH_2$ | 4 | 1851 |
| Indol-$K^{12}$-$NH_2$ | $H_2N$-ILPWKWPWWPWK-$CONH_2$ | 5 | 1723 |
| Indol-$R^{12}$-OH | $H_2N$-ILPWKWPWWPWR-OH | 6 | 1752 |
| Indol-$R^{12}K^{13}$-$NH_2$ | $H_2N$-ILPWKWPWWPWRK-$CONH_2$ | 7 | 1880 |
| | $H_2N$-ILPWKWPWW-$CONH_2$ | 8 | |
| | $H_2N$-ILPWKWPWW-OH | 9 | |
| | $H_2N$-LPWKWPWWPWRR-$CONH_2$ | 10 | |
| | $H_2N$-PWKWPWWPWRR-$CONH_2$ | 11 | |
| | $H_2N$-WKWPWWPWRR-$CONH_2$ | 12 | |
| | $H_2N$-KWPWWPWRR-$CONH_2$ | 13 | |

*theoretical molecular weights were identical to those determined by mass spectrometry.
**indolicidin (naturally occurring).

In general, indolicidins useful in accordance with the present invention have the general structure $H_2$N-I-L-P-W-K-W-P-W-W-P-W-X (SEQ ID NOS:14 and 15), where X designates one or two independently selected amino acids.

Indolicidins typically contain twelve or thirteen amino acids and are tryptophan-rich. Indolicidin, for example, has a tryptophan content of about 38 percent (5/13 residues). In nature, each amino acid occurs in proteins in a characteristic expected proportion. Tryptophan is the least frequently used amino acid in naturally occurring proteins, with an average occurrence of about 1 percent (Clapper (1977) *Biochem. Biophys. Res. Comm.* 78: 1018–1024). Thus, a tryptophan-rich sequence as defined herein can be readily identified by containing a proportion of tryptophan residues greater than about 10%, preferably greater than about 20%.

Indolicidins are further characterized by having substantially the same sequence as naturally occurring indolicidin. As used herein, the term "substantially the same sequence" means that the peptide sequence of an indolicidin analog is at least 60%, preferably 70%, more preferably 80%, homologous with the sequence of indolicidin (SEQ ID NO: 1). Thus, a limited number of modifications can be made to the indolicidin peptide sequence to obtain indolicidins that have a desirable antimicrobial selectivity such as increased antimicrobial activity or decreased hemolytic activity as compared to naturally occurring indolicidin. For example, an indolicidin analog can have the same peptide sequence as indolicidin but can be modified, for example, by containing a C-terminal reactive group other than an amide, which is found in naturally occurring indolicidin (see, for example, SEQ ID NO: 5).

Modifications to the indolicidin peptide sequence also can include, for example, additions, deletions or substitutions of amino acids, provided the indolicidin analog produced by such modifications is tryptophan-rich and has substantially the same structure of naturally occurring indolicidin as defined herein. Analogs that are amidated and/or possess a dibasic dipeptide at the C-terminus are preferred.

The indocidin peptides of the present invention can be present in the formulation with free termini or with amino-protected (N-protected) and/or carboxy-protected (C-protected) termini. Suitable N-terminal amino protecting groups include: (a) aromatic urethane-type protecting groups which include benzyloxycarbonyl, 2-chlorobenzyloxycarbonyl, 9-fluorenylmethyloxycarbonyl, isonicotinyloxycarbonyl and 4-methoxybenzyloxycarbonyl; (b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which include adamantyloxycarbonyl, cyclopentyloxycarbonyl, cyclohexyloxycarbonyl and isobornyloxycarbonyl; (d) acyl protecting groups or sulfonyl protecting groups. Preferred protecting groups include benzyloxycarbonyl, t-butoxycarbonyl, acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl. Protecting groups for the N-terminal amino group of amino acids and peptides such as those disclosed above are well known in the art. See Bodanszky, N., Peptide Chemistry, pp. 74–103, Springer-Verlag, New York (1988) and references cited therein.

Suitable the C-terminus is protected with a carboxy terminal residue which is preferably homoserine (Hse), homoserine lactone, homoserine amide, or a C1–C8 alkyl (preferably C1–C4 alkyl), secondary or tertiary amides of homoserine. When Hse containing analogs are desired, the indolicidin peptides are first synthesized with a Met incorporated on the C-terminus. This Met residue is then modified with cyanogen bromide after HF cleavage by methods well known in the art. This cyanogen bromide cleavage converts the Met to the C-terminal Hse lactone peptide. This can be converted to the Hse amide peptide by treatment with the appropriate amine in a solvent such as methanol or dimethylformamide.

Particularly preferred indolicidins range in length from 8 to 45 amino acids, preferably from 9 to 22 amino acids and most preferably from 10 to 13 amino acids. The indolicidin concentration ranges from about 3.125 µg/ml to about 100 µg/ml, more preferably about 4 µg/ml to about 50 µg/ml, still more preferably about 5 µg/ml to about 32 µg/ml, and most preferably about 8 to about 16 µg/ml.

The indolicidins can be used individually or combinations of different indolicidins can be used together in the solutions of this invention.

2) Buffers

The ophthalmic solutions of this invention are preferably formulated in a buffer system (buffer solution) to regulate pH, and tonicity in a range compatible with ophthalmic use and with optimum activity of the indolicidin(s) present in the solution. The buffer is also preferably selected for compatibility with application to a mammalian eye. Thus, it is typically neither too acidic nor too basic and is formulated with physiologically compatible salts. Typically sufficient quantities of buffering agent are employed to maintain activity of the peptide and of any enzymes employed, typically in a formulation to effect a neutral or slightly alkaline pH.

It was a surprising discovery of this invention that the most widely used buffer systems for ophthalmic solutions, e.g., saline buffer systems such as phosphate buffered saline (PBS), significantly degrades the activity of the indolicidin and are thus not well suited for use in indolicidin-based ophthalmic solutions.

More broadly it was a discovery of this invention that, in general, solutions containing physiologically relevant concentrations of halide ions (e.g., Cl⁻, Br⁻, Fl⁻), degrade indolicidin activity. It was also, however, a discovery of this invention that Good's buffers (e.g., TRIS, PIPES, HEPES, etc.) will maintain indolicidin activity even in the presence of physiological concentrations of halide ion.

Thus, in a preferred embodiment, the buffers used in this invention include either buffers having a substantially reduced (e.g., less than 0.85 wt % more preferably less than about 0.75 wt %, and most preferably less than about 0.5 wt % halide ion concentration). Particularly preferred buffers have substantially no halide ion. Such buffers include, but are not limited to phosphate buffers (e.g sodium or potassium phosphate), carbonate buffers, borate buffers, acetate buffers, citrate buffers, bicarbonate buffers and the like. Particularly preferred buffering agents are phosphate buffers (e.g., sodium phosphate buffers) and alkali metal borates such as sodium or potassium borates. Additionally, other pH adjusting agents may be employed such as inorganic acids.

It is known that boric acid or other borate buffers possess the additional feature of microbistatic inhibition in the presence of low concentrations of microbes. therefore, borate buffers are commonly used in the packaging solution of contact lenses. For example, 0.5% by weight of boric acid and 0.052% by weight of sodium borate is known as an effective amount for microbistatic inhibition.

In another preferred embodiment, the buffer is a Good's buffer. Preferred Good's buffers for use in this invention include, but are not limited to: ADA, PIPES, ACES, BES, MOPS, TES, HEPES, EPPS, Tricine, Bicine, CHES, and CAPS (see, e.g., Good et al. (1966) *Biochem.*, 5: 467–477), with TRIS being most preferred. Where a Good's buffer is used, a halide ion can be present in a concentration less than 0.85 wt %.

Ideally, the pH of the buffer and hence the pH of the ophthalmic solution is neutral to slightly alkaline. The determination of a preferred pH range for any given indolicidin can readily be carried out by known techniques. It is preferred to manipulate the working solution to an optimum pH range for a given indolicidin, but such is not an absolute requirement. Generally, it is preferred that the ophthalmic solution have a pH between about 5 to 9, more preferably between about 7 and 8.5 and most preferably between about 7.2 to about 7.5.

The buffer concentration broadly establishes the tonicity of the solution. The buffer is generally present in a concentration no greater than about 100 mM, and preferably ranges in concentration from about 0.1 to about 5 mM, more preferably from about 0.5 to about 15 mM, and most preferably from about 1–10 mM.

The choice of the particular buffer system depends on the particular application(s) intended for the ophthalmic solution. Methods of preparing such buffers are well known to those of ordinary skill in the art and can be found, for example in any of a number of standard laboratory manuals (see, e.g., Sambrook et al. (1989) *Molecular Cloning: A Laboratory Manual,* Cold Spring Harbor Press). In addition, such buffers are commercially available from a wide variety of manufacturers (see, e.g., Sigma, St. Louis, Mo.). The buffer solutions are preferably formulated as sterile solutions. However, the microbicidal activity of the indolicidin(s) renders the solutions essentially self-sterilizing. Thus, in some embodiments, the solutions can be formulated without sterilization.

3) Tonicity adjusting agent.

While the buffer itself is a "tonicity adjusting agent" and a "pH adjusting agent" that broadly maintains the ophthalmic solution at a particular ion concentration and pH, additional "tonicity adjusting agents" can be added to adjust or "fine tune" the final tonicity of the solution. Such tonicity adjusting agents are well known to those of skill in the art and include, but are not limited to mannitol, sorbitol, dextrose, sucrose, urea, and glycerin. Also, various salts, including halide salts of a monovalent cation (e.g., NaCl, KCl, etc.) can be utilized, however, to preserve indolicidin activity the use of such halide salts is preferably confined to incorporation in Good's buffers (e.g., TRIS).

The tonicity adjusting agent, when present, is preferably in a concentration ranging from 0.1 to 1 wt %, more preferably 0.5 to 1.0 wt %, and most preferably 0.8 to about 0.9 wt %. In embodiments where a tonicity adjusting agent is present the solution can contain a single agent or a combination of different tonicity adjusting agents.

4) Surfactants/detergents.

Where the ophthalmic solution is to be used for lens cleaning, the solution pre ferably contains one or more surfactants. Suitable surfactants can include cationic, anionic, non-ionic or amphoteric surfactants, so long as the surfactant passes the critical micelle test see Example section). Preferred surfactants are neutral or nonionic surfactants.

Nonionic surfactants in accordance with the present invention include non-ionic block copolymers, preferably members of the group known as poly(oxyethylene)-poly(oxypropylene) block copolymers (also known as poloxamers) available under tradenames such as PLURONIC and EMKALYX. Such copolymers are known commercially and are produced in a wide range of structures and molecular weights with varying contents of ethylene oxide. These non-ionic surfactants are non-toxic, stable and readily dispersible in aqueous systems and are compatible with a wide variety of formulations and other ingredients for ophthalmic preparations. Further, poloxamers are well suited to ophthalmic applications as they generally afford minimal or no eye irritation. One class of poloxamer well suited for use in the ophthalmic solutions of this invention is a specific class of polyethyleneoxy-polypropyleneoxy block copolymer adducts of ethylene diamine (also known as poloxamine), which agents are both effective at cleaning and exhibit minimal or no eye irritation (see, e.g. U.S. Pat. No. 4,820,352).

Examples of suitable surfactants include, but are not limited to, polyethylene glycol esters of fatty acids, polyoxypropylene ethers of C12–C18 alkanes and polyoxyethylene, polyoxypropylene block copolymers of ethylene diamine (i.e., poloxamine). Particularly preferred surfactants include poloxamer 182LF, poloxamer 188, poloxamer 331, poloxamer 407NF, sodium lauryl sulfate, pluronic F-127, Povidone (Sigma), PVP k-30, hydroxyethyl cellulose, NF and Tyloxapol (Sigma).

The surfactant, when present, is preferably in a concentration that ranges from about 0.01 to about 3 wt %, more preferably from about 0.1 to about 1.5 wt %, and most preferably from about 0.25 to about 0.5 wt %. Where used, the surfactant can include a single surfactant or a combination or surfactants.

5) Chelating agent.

In certain embodiments, the activity of the indolicidin and/or the shelf-life of the ophthalmic solution can be enhanced by the inclusion of one or more cation chelating agent, more preferably a chelator of divalent cations. Chelating agents are well known to those of skill in the art. Preferred chelating agents include, but are not limited to, ethylenediaminetetraacetic acid (EDTA) and its salts (e.g., disodium), ethylenebis(oxyethylenenitrilo)tetraacetic acid (EGTA), and 2,2'-(ethylenediimino)-dibutyric acid EDBA which are normally employed in amounts from about 0.01 to about 0.2 wt %, more preferably from about 0.1–0.2 wt %, and most preferably about 0.025 to about 2.0% wt %. Other known chelating (or sequestering agents) such as certain polyvinyl alcohols can also be employed.

6) Divalent cations.

In certain preferred embodiments, the ophthalmic solutions of this invention can optionally include one or more species of divalent cation. Without being bound to a particular theory, it is believed that the presence of divalent cations can inhibit growth of certain gram negative bacteria. Preferred divalent cations include, but are not limited to $Mg^{2+}$, $Ca^{2+}$, $Zn^{+2}$, $Fe^{+2}$, and $Ba^{2+}$, with $Mg^{2+}$ being most preferred.

The divalent cation, when present, is at a concentration ranging from about 20 mM to about 50 mM.

7) Bacteriostatic adjuvant

Normally, a preservative (bacteriostatic adjuvant), other than the indolicidin, is not added to the compositions of the present invention. Thus, rinsing of the lens after contact with the composition is not required. A preservative may be added for the purpose of reducing the necessary concentration of indolicidins, particularly where the solution is not expected to come into direct contact with the eye. It is noted however, that many such preservatives are eye irritants and/or toxic. If preservatives are employed, the contact lens is preferably rinsed prior to insertion into the eye.

Thus, in a further embodiment, one or more additional antimicrobial agents and/or other cleaning/disinfecting agents can be used in combination with the indolicidins, so long as they do not adversely effect the indolicidin's antimicrobial activity and, if toxic, do not come into contact with the mouth and/or skin and/or eye. Suitable preservatives include, but are not limited to chlorhexidine, thimerosal, PHMB (polyhexamethylene biguanide), boric acid, borate salts, potassium sorbate and sodium sorbate, benzalkonium chloride and other quaternary ammonium salt, guanidine salt such as chlorhexidine and polyhexamethylene biguanide, or formaldehyde donor, benzalkonium chloride, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, polyquad, potassium benzoate, propylparaben, propylparaben sodium, sodium benzoate, sodium dehydroacetate, sodium propionate, sorbic acid, sodium perborate, thymol, and antimicrobial polypeptides (e.g., a crecropin, a defensin, and a magainin), and mixtures thereof. Typically use of the halide salt antimicrobial agents will be limited to incorporation in Good's buffers. The preservatives, when present, are in a concentration ranging from about 0.01 wt % to 2.5 wt %, more preferably from about 0.1 wt % to about 1.0 wt %, and most preferably from about 0.2 wt % to about 0.5 wt %.

8) Demulcent

The ophthalmic solutions can optionally include a demulcent. Demulcents are substances that soothe irritated tissue, particularly mucous membranes. Demulcents (or humectants) are used for lubricating mucous membrane surfaces and for relieving dryness and irritation. The term "demulcent", as used herein is intended to mean an agent, usually a water-soluble polymer, which is applied topically to the eye to protect and lubricate mucous membrane surfaces and relieve dryness and irritation. Within this meaning, the term "wetting agent" is also commonly used. Furthermore, it will be understood that some constituents possess several functional attributes. For example, cellulose derivatives are common demulcents, but are also used as "viscosity increasing agents". Similarly, glycerin is a known demulcent but is also used as a "tonicity adjusting agent". Examples of the most widely used demulcents include: polyvinyl alcohol, polyvinyl pyrrolidone, cellulose derivatives and polyethylene glycol.

"Over-the-counter" use of demulcents within ophthalmic compositions is regulated by the US Food & Drug Administration. For example, the Federal Register (21 CFR Part 349) entitled Ophthalmic Drug Products for Over-the-Counter Use: Final Monograph list the accepted demulcents along with appropriate concentration ranges for each. Specifically, §349.12 list the following approved "monograph" demulcents: (a) cellulose derivatives: (1) carboxymethylcellulose sodium, (2) hydroxyethyl cellulose, (3) hydroxypropyl methylcellulose, methylcellulose, (b) dextran 70, (c) gelatin, (d) polyols, liquid: (1) glycerin, (2) polyethylene glycol 300, (3) polyethylene glycol 400, (4) polysorbate 80, (5) propylene glycol (e) polyvinyl alcohol, and (f) povidone (polyvinyl pyrrolidone). §349.30 further provides that in order to fall within the monograph, no more than three of the above-identified demulcents may be combined.

Specific examples of known ophthalmic compositions comprising various demulcents are know to those of skill in the art. For example, U.S. Pat. No: 5,591,426 discloses an ophthalmic solution useful as an artificial tear. The reference includes a specific example of a borate buffered, preserved (e.g., benzalkonium chloride), aqueous solution including the following three demulcents: 1) glycerin, 2) polyvinyl pyrrolidone, and 3) a cellulose derivative, e.g., hydroxypropyl methyl cellulose. U.S. Pat. No. 5,106,615 discloses isotonic humectant eyedrops including glycerin, polyethylene glycol, or propylene glycol with an anionic polymer such as Carbomer 941. Other references disclose the use of various combinations of demulcents including, but not limited to propylene glycol, polysorbate 80, polyvinyl pyrrolidone, polyethylene oxide, polystyrene sulfonate, and polyacrylamide, hydroxy ethyl cellulose, polyethylene glycol 6000, and dextrose (see, e.g., U.S. Pat. Nos: 4,029,817, 3,767,788; 3,767,789; 3,856,919; 3,907,985; 3,920,810; 3,947,573; 3,987,163, 3,549,747, 4,131,651, 4,120,949, and 4,409,205

9) Viscosity adjusting agent.

In another embodiment, the ophthalmic solutions of this invention can optionally include viscosity adjusting agents (e.g., particularly when the ophthalmic solution is intended to act as a lubricant (i.e., artificial tear)). Suitable viscosity adjusting agents for administration to an eye are well known to those of skill in the art. In particular, Cellulose derivatives are commonly used to increase viscosity, and as such, offer other advantages. Specific cellulose derivatives include, but are not limited to hydroxypropyl methyl cellulose, carboxymethyl cellulose, methyl cellulose, hydroxyethyl cellulose, etc.

Typically, particularly when used as an artificial tear, the ophthalmic solution has a viscosity from about 1 to about 50 cps. As a solution, the subject composition is usually dispensed in the eye in the form of an eye drop. It should be understood, however, that the subject composition may also be formulated as a viscous liquid (i.e. viscosities from 50 to several thousand cps), gel, or ointment. Furthermore, in some contact lens related embodiments, lenses may be soaked or otherwise exposed to the subject composition prior to wear.

10) Other components.

The present contact lens cleaning solution may further contain, as needed, various other known components which are generally used for cleaning and maintenance of contact lenses as long as the components are compatible with the antimicrobial activity of the indolicidin(s) present in the solution. Thus, for example, where the solution is intended for lens cleaning purposes, it can additionally include various tertiary amine oxide or oxides. The solution can additional include effervescing agents (e.g., sodium bicarbonate) microabrasives (e.g., polymer microbeads), and various medicinal agents (e.g., antibiotics as might be used in the treatment of eye infections).

III. Preparation of Indolicidin Formulations

A) Indolicidin Synthesis

Indolicidins are commercially available (see, e.g., Peninsula Laboratories, Belmont, Calif.). Alternatively the indolicidins can be synthesized either by chemical synthesis methods (i.e. peptide synthesis) or by biological synthesis (e.g., recombinant expression systems).

1) Chemical synthesis.

Indolicidins can be chemically synthesized in solution or on a solid support using well known methods of peptide synthesis. Solid phase synthesis in which the C-terminal amino acid of the sequence is attached to an insoluble support followed by sequential addition of the remaining amino acids in the sequence is a preferred method for the chemical synthesis of the indolicidin polypeptides of this invention. Techniques for solid phase synthesis are described by Barany and Merrifield, Solid-Phase Peptide Synthesis; pp. 3–284 in *The Peptides: Analysis, Synthesis, Biology.* Vol. 2: *Special Methods in Peptide Synthesis,* Part A., Merrifield et al. (1963) *J. Am. Chem. Soc.,* 85: 2149–2156, and Stewart et al. (1984) *Solid Phase Peptide Synthesis,* 2nd ed. Pierce Chem. Co., Rockford, Ill.

Typically indolicidin analogs are synthesized using an automated peptide synthesizer such as a Milligen 9050 (Milford, Mass.), although manual methods of composition peptide synthesis also can be used. When automated methods of peptide synthesis were used, indolicidin analogs are preferably synthesized on a polyethylene glycolpolystyrene (PEG-PS) graft resin and using $N^\alpha$-Fmoc amino acid derivatives as described in U.S. Pat. No. 5,547,939. In addition, a suitable linker such as a peptide amide linker (PAL; 5-(4-Fmoc-aminomethyl-3,5-dimethoxyphenoxy)valeric acid; Fmoc is 9-fluorenylmethyloxy-carbonyl; Milligen) can be used to create carboxamide end groups. Other resins, amino acid derivatives and methods of modifying amino acid reactive groups can be used to obtain the desired indolicidin analog.

A newly synthesized peptide can be manipulated while still attached to a resin or can be removed from the resin and then modified. Methods for modifying the N-terminus or C-terminus of a peptide are well known in the art and include, for example, amidation of the C-terminus and, if desired, acetylation of the N-terminus (see, for example, *Protein Engineering. A practical approach* (IRL Press 1992); and Bodanszky, *Principles of Peptide Synthesis* (Springer-Verlag 1984)). Similarly, methods for modifying the reactive side chain of an amino acid are well known in the art of peptide synthesis.

2) Biological synthesis.

In a preferred embodiment, the indolicidin polypeptides, or subsequences thereof, are synthesized using recombinant DNA methodology. Generally this involves creating a DNA sequence that encodes the indolicidin, placing the DNA in an expression cassette under the control of a particular promoter, expressing the protein in a host, isolating the expressed protein and, if required, renaturing the protein.

DNA encoding the indolicidin proteins or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al.(1 979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In one embodiment, indolicidin proteins of this invention can be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired indolicidin sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the known sequence information for indolicidins. Appropriate restriction sites can also be added to the nucleic acid encoding the indolicidin protein or protein subsequence by site-directed mutagenesis. The plasmid containing the indolicidin sequence or subsequence is cleaved with the appropriate restriction endonuclease and then ligated into the vector encoding the second molecule according to standard methods.

The nucleic acid sequences encoding indolicidin proteins or protein subsequences may be expressed in a variety of host cells, including *E. coli,* other bacterial hosts, yeast, and various higher eukaryotic cells such as the COS, CHO and HeLa cells lines and myeloma cell lines. As the indolicidin proteins are typically found in prokaryotes, a prokaryote host is preferred. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant indolicidin proteins can be purified according to standard procedures of the art, including ammonium sulfate precipitation, affinity columns, column chromatography, gel electrophoresis and the like (see, generally, R. Scopes, (1982) *Protein Purification,* Springer-Verlag, N.Y.; Deutscher (1990) *Methods in Enzymology Vol. 182: Guide to Protein Purification.,* Academic Press, Inc. N.Y.). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill in the art would recognize that after chemical synthesis, biological expression, or purification, the indolicidin protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, Debinski et al. (1993) *J. Biol. Chem.,* 268: 14065–14070; Kreitman and Pastan (1993) *Bioconjug. Chem.,* 4: 581–585; and Buchner, et al., (1992) *Anal. Biochem.,* 205: 263–270). Debinski et al., for example, describes the denaturation and reduction of inclusion body proteins in guanidine-DTE. The protein is then refolded in a redox buffer containing oxidized glutathione and L-arginine.

One of skill would recognize that modifications can be made to the indolicidin proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

B) Compounding of Formulations

In a preferred embodiment, the ophthalmic compositions of this invention are formulated and stored as aqueous solutions. While the components described above are selected so as to be readily soluble or miscible in an aqueous solution, it was a discovery of this invention that the indolicidin'(s) activity decreases if they are added directly to a buffer solution (e.g., potassium phosphate buffer).

Thus, in a preferred embodiment, the indolicidin is solubilized in water prior to preparing a stock solution that is then added to the buffer. Thus, for example, as illustrated in the Examples, herein, a 5,000 $\mu$g/ml stock indolicidin (e.g., L-IND) solution was prepared in water by weighing out 5 mg and dissolving it in 1 ml water. The tube was inverted to dissolve the polypeptide. The stock was diluted 2-fold in water to prepare 10x concentrated stock solutions: 2500, 1250, 625, 312, 160, 80, 40, 20, and 10 $\mu$g/ml or the stock was diluted 1:10 in water or sodium phosphate buffer followed by the 2-fold dilution series resulting in a 1x or working concentration series of L-IND.

C) Optimization of Formulations

As indicated above, the ophthalmic solution can be prepared by suspending or dissolving the indolicidins (after solubilization) into the buffer. The amount of antimicrobial peptide used in the ophthalmic composition of the present invention is dependent on the intended use of the solution. The concentration of indolicidin will be lowest in compositions intended for use as eye drops, higher for compositions intended for cleaning solutions, higher yet for compositions intended as disinfecting or storage solutions, and highest for compositions intended for sterilization.

In general, a minimum effective amount of indolicidin is that which will at least partially reduce the microorganism population on the lens (either corneal or contact lens) being treated. Preferably, an effective amount is that which will reduce the microbial burden by at least three log orders for bacteria and at by least one log order for yeasts and molds in a time span of from about four to about twenty four hours, more preferably two to four hours for bacteria and twelve to eighteen hours for yeast.

For compositions intended for disinfecting, storage or cleaning, a typical amount of indolicidin is greater than about 12.5 $\mu$g/mL of solution, preferably greater than about 25 $\mu$g/mL, more preferably greater than about 50 $\mu$g/mL. The indolicidin is typically present in concentrations from about 1 to 100, preferably 1 to 50, more preferably 4 to 25 ppm. Typically, the ophthalmic composition contains about 0.0001% to 0.01% weight to total volume of composition, of indolicidin.

While preferred ranges are provided, in particularly preferred embodiments, the concentrations of various components, in particular the indolicidin concentration and the surfactant concentration (when surfactant is present) are optimized for a particular indolicidin/buffer combination.

Optimal indolicidin concentration can be ascertained by determining MIC values and ensuring that there is sufficient indolicidin to achieve a preferred microbicidal activity as indicated above. Methods of performing such assays are illustrated in the Examples, particularly in Example 10.

Optimization of the other components can also be accomplished for a particular indolicidin and buffer system. Thus, for example, in a preferred embodiment containing a surfactant, the surfactant concentration is in excess of the "critical micelle concentration; the concentration that must be reached in order that micelles are formed is called the critical micelle concentration. Methods of determining critical micelle concentration are described in Example 1.

Additional components may be added to or incorporated in the composition, provided the additives do not substantially decrease the antimicrobial activity of the indolicidins in the composition as described above. Typical components and preferred ranges are provided above.

In one particularly preferred embodiment the solution is compounded to provide broad spectrum antimicrobial activity. Solutions formulated in accordance with this embodiment comprise an indolicidin, a phosphate buffer, and a surfactant (e.g. Pluronic).

In other preferred embodiments, the solution is formulated to provide narrow-spectrum antimicrobial activity against particular pathogens. These embodiments, typically utilize a Goods buffer (rather than a phosphate buffer.) Preferred formulations include Tris buffer present in a concentration of from 1–10 mM.

The compositions of the invention are stable for long periods of time. Preferred compositions retain 100% antimicrobial activity for at least 6 months at temperatures ranging from 40° F. to 80° F.

D) Alternative Formulations

While the ophthalmic solutions of this invention are preferably formulated as "ready for use" aqueous solutions, alternative formulations are contemplated within the scope of this invention. Thus, for example, the indolicidin(s), surfactants, salts, chelating agents, or other components of the ophthalmic solution, or mixtures thereof, can be lyophilized or otherwise provided as a dried powder or tablet ready for dissolution (e.g., in deionized, or distilled) water. Because of the self-preserving nature of the solution, sterile water is not required.

In a preferred embodiment, formulation of the compositions of this invention in dry power or tablet formats involves protection of the protein(s) present. Effective formulations of the compositions of this invention typically involve (i) processing and formulating the protein, and other agents if present, so that the protein's conformation and biological activity are maintained throughout processing and during prolonged release from the dry form.

Sustained protein "packaging" systems can be achieved with a variety of microsphere delivery systems often used for in vivo delivery of protein therapeutics. In one preferred embodiment, the ProLease biodegradable microsphere delivery system for proteins and peptides (Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the protein in a polymer matrix that can be compounded as a dry formulation with or without other agents.

The ProLease microsphere fabrication process was specifically designed to achieve a high protein encapsulation efficiency while maintaining protein integrity (Gombotz, et al. (1991) U.S. Pat. No. 5,019,400). The process consists of (i) preparation of freeze-dried protein particles from bulk protein by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the protein, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

IV. Uses of Indolicidin-based Ophthalmic Solutions

The ophthalmic solutions of this invention may be applied to or used in conjunction with any kinds of contact lens including, but not limited to hard contact lenses (e.g., mainly made of methyl methacrylate), oxygen permeable contact lenses, non-water swellable, or absorbable soft contact lens, etc. Further, the ophthalmic solutions may be used irrespective of whether the contact lens is colored or non-colored.

As indicated above, the solutions of this invention are useful for a wide variety of activities in the packaging, processing, shipping, storing, and care of contact lenses. Thus, for example, the indolicidin-based solutions can be used for disinfection of contact lenses, contact lens containers such as carrying cases, vials, and shipping containers (e.g., blister packs). These various containers are typically composed of polycarbonate, polyethylene, polytetrafluorethylene (PTFE), polyvanillidinefluoride (PVF), and polypropylene.

In addition, the solutions can be used for cleaning, storage and rehydration of contact lenses. The solutions can be compounded as "artificial tears" for direct application to the eye to rehydrate, lubricate, and disinfect the lenses in place, and the solutions can be used as a "medicament" to reduce microbial flora on the surface of the eye. In this latter case, the solutions can be additionally compounded with one or more medicaments used in the treatment of inflammation, infection, or other pathology of the eye as described below.

A) Method of Disinfecting a Contact Lens

The compositions according to the present invention are employed in an effective amount to disinfect the contact lens being treated in a selected length of time. The contact lens is contacted with the ophthalmic composition containing the indolicidin for the desired length of time, rinsed (with either the ophthalmic solution or with saline), and inserted into the eye of the user.

The contact lens is typically contacted with (or soaked in) the ophthalmic composition for a time sufficient is to at least partially reduce the microorganism population on the lens being treated. Preferably, the time is sufficient to reduce the microbial burden by at least three log orders for bacteria and by at least one log order for yeasts and molds. Typically, the lens is soaked in the ophthalmic composition for at least about 2 hours, preferably for at least about 4 hours, more preferably at least about 6 hours, and most preferably overnight. In any event, effective disinfecting times for any given composition within the present invention can be readily determined through routine testing (see for example, "Guidance for Industry. Premarket Notification (510(k)) Guidance Document for Contact Lens Care products," May 1, 1997, U.S. Department of Health and Human Services, Food and Drug Administration, Center for Devices and Radiological Health). Mild agitation may be required for a period of about 10 to 45 seconds for optimal mixing and contact.

Preferably, the contact lens treated according to the invention can be removed from the solution and used without the need for a separate washing step. For example, contact lenses can be rinsed with the same ophthalmic solution containing the indolicidin prior to insertion into the eye. Thus, there is no need for a separate rinsing step with, for example, a saline solution. However, rinsing may be required in the case where a preservative is included in the ophthalmic composition. In which case, the contact lens is preferably washed with a saline solution.

B) Contact Lens Packaged without Autoclaving

The solutions of this invention are useful for disinfecting of essentially any container used to hold one or more contact lenses. Thus, in one embodiment, contact lens packaging (e.g., storage containers such as vials or lens cases or shipping/packaging containers such as vials, capsules, blister packs, and the like) can be rinsed with the solution prior to insertion of the lens. Because of the high microbicidal activity of the solutions of this invention, however, the packages need not be pre-rinsed. They can simply be filled with he solution before, during, or after placement of the lens in the package. Where the lens is held for long term storage (e.g., whole sale packaging), or storage, the solutions may be formulated with relatively high indolicidin concentrations (e.g., 50–100 $\mu$g/ml) and may contain additional non-indolicidin preservatives.

C) A Synthetic Tear and Ocular Lubricant

In still another embodiment, the solutions of this invention can be administered (e.g., from a drop bottle or eyewash) directly to the contact lens on the surface of the eye. In this context, preferred formulations will act as an artificial tear that aids to re-wet the lens and eye, rehydrate the lens, afford additional lubrication, and reduce irritation or inflammation of the eye or surrounding tissue. As indicated above, solutions for this use may additionally include viscosity increasing agents and/or demulcents.

In a typical application, the ophthalmic solution is provided in a convenient applicator (e.g., an eye drop bottle) for administration directly to the eye. The user then typically applies one or two drops to each eye (followed by blinking to disperse the solution) as needed.

V. Kits

In still another embodiment, this invention provides kits for the packaging and/or storage and/or care and/or use of contact lenses where the kits utilize one or more of the ophthalmic solutions described herein. Thus, for example, preferred kits comprise one or more containers containing one or more ophthalmic solutions, tablets, or capsules of this invention. The kits can be designed to facilitate one or more aspects of contact lens production, shipping, use, and storage. Thus, for example, the kit can comprise a contact lens shipping package (e.g., vial or blister pack), a storage case, a cleaning vial or case, and the like.

The kits may optionally include instructional materials containing directions (ie., protocols) disclosing means of use of the indolicidin-based ophthalmic solutions provided therein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g. CD ROM), and the like. Such media may include addresses to internet sites that provide such instructional materials.

The following examples are presented for illustrative purposes and are not intended to limit the scope of this invention

EXAMPLES

The following examples are offered to illustrate, but not to limit the claimed invention.

Example 1

Protocols and Assays Used for the Evaluation of Indolicidin-Based Ophthalmic Solutions A) Protocol # 1: Comparative Efficacy of L-indolicidin and Three Commercial Lens-care Solutions This protocol is used to develop dose-response (kill) curves to calculate the minimal inhibitory concentration of an indolicidin (e.g., L-indolicidin (L-IND)) when formulated in a commercially available phosphate buffered saline (PBS) solution. In addition, for comparative purposes, kill curves are established for the following three commonly available commercial lens-care products containing different preservatives:

1) Softwear (Ciba Vision)—Sterile, isotonic, saline solution containing sodium chloride and an antimicrobial buffer system (ABS) consisting of boric acid, sodium borate, and sodium perborate (generating up to 0.006% hydrogen peroxide stabilized with phosphonic acid); Lot 61443; expiration date: December 1999.

2) Opti-Free (Alcon)—Sterile, buffered, isotonic, aqueous solution with sodium citrate and sodium chloride with edetate disodium (0.05%) and polyquaternium-1 (0.001%) as preservatives; Lot AAY9; expiration date: September 1998.

3) AOSept (American Optical)—Sterile ophthalmic solution containing microfiltered hydrogen peroxide (3%), sodium chloride (0.85%) stabilized with phosphonic acid, and buffered with phosphates; Lot 62453; expiration date: January 1999.

These three products serve as control samples. In addition a commercial saline solution without preservatives for soft contact lenses is also tested. The brand that used is:

4) Longs Non-Preserved Saline Solution (Longs)—Sterile, aqueous, isotonic solution of sodium chloride buffered with boric acid and sodium borate (respective concentrations not specified); Lot 5V006; expiration date: August 1997.

Since boric acid and sodium borate are known to possess antimicrobial activity, the Longs Non-Preserved Saline Solution is tested at just one dose level, namely full strength, to determine if the buffering components have antimicrobial activity.

Stock solutions were prepared as follows: For L-IND, a stock solution of 10 mg/ml was prepared and shipped to the inventors on dry ice. The stock solution was kept frozen at −4° C. The "Softwear", "Opti-Free", and "AOSept" stock solutions consisted of the undiluted solution (full strength). The "Longs Non-Preserved Saline Solution" was tested at full strength only.

An initial dose range experiment is performed to determine a suitable dose range for the final experiment. The indolicidin (e.g., L-IND) is tested in the preliminary toxicity experiment at 13 different dose levels in a range between 500 $\mu$g/ml and 0.125 $\mu$g/ml. The 3 control samples with preservatives are tested at 13 different dose levels with the highest dose level representing the undiluted solution. A total of 12 serial 2-fold dilutions are made from the undiluted control solutions. The Longs Non-Preserved Saline Solution is tested at full strength only.

A subsequent experiment is performed with at least 8 dose levels which are selected from the initial range finding experiment such that a kill curve can be established with at least two non-toxic dose levels representing the two highest non-toxic dose levels.

The stock solutions are diluted in a 2-fold fashion by transferring 1 ml of each stock solution to 1 ml of appropriate diluent in sterile glass tubes (100×13 mm). Twelve additional 2-fold dilutions are made by transferring 1 ml aliquots of each dilution to 1 ml diluent. The diluent for all commercial lens-care products is PBS.

*Pseudomonas aeruginosa* (ATCC 27853) obtained directly from the American Type Culture Collection is used as a test organism. The bacterium is grown overnight at 37° C. in DIFCO nutrient broth. The overnight culture is washed two times in sterile PBS by centrifugation at 7,000 RPM. The cells are resuspended in sterile PBS and diluted to give an estimated $5\times10^5$ colony-forming-units (CFU) per 10 $\mu$l.

To each of the dilution tubes containing 1 ml of PBS with the test chemical is added 10 $\mu$l of the diluted cell suspension to give in the 1 ml final volume the equivalent of a cell density of $5\times10^5$ CFU. Negative vehicle control consists of the diluent with bacteria only. The tubes are then be incubated at 37° C. for 1 hour after which time they are placed on ice.

Viable counts of the bacteria are performed by 10-fold serial dilutions in sterile PBS and by plating 0.1 ml aliquots on nutrient agar plates. One plate for each dilution is used in the preliminary assay while two plates per dilution are used in the final experiment. The plates are incubated overnight at 37° C. and colonies are counted and recorded. Regular glass pipettes are used for all handling (diluting and plating) of the test and control samples, since it is believed that L-IND may adhere to plastic pipettes.

Survival is expressed as number of surviving bacteria (CFU/ml) for each dilution of the test article and control solutions. The lowest dose of the test article that results in complete kill of the test organism, compared to the non-exposed control, is determined to be the MIC value.

B) Protocol # 2: Efficacy Determination for Cationic Antimicrobial Peptides by a Modified Microtiter Broth Dilution Method The objective of this protocol is to establish a modified testing procedure recommended specifically for susceptibility testing of cationic antimicrobial peptides. This procedure was introduced at the 1996 International Conference on Antimicrobial Agents and Chemotherapeutics (ICAAC). The method is based on the classical microtiter broth dilution recommended by the National Committee of Laboratory Safety and Standards (NCLSS) as published by Amsterdam (1996) *Susceptibility Testing of Antimicrobials in Liquid Media,* In: *Antibiotics in Laboratory Medicine,* Lorian V., Ed. Fourth Edition, pp.52–111. Williams and Wilkins, Baltimore. The procedure described below is a modification of the recommended procedure referenced above.

It is important that the indolicidin (e.g, L-IND) not come in contact with untreated glass or polystyrene as cationic peptides bind to these materials. Glass coated with Sigmacote or materials made of polypropylene are recommended for testing these peptides.

The materials utilized included sterile glass tubes containing 5 ml of Mueller-Hinton Broth (MHB), Mueller-Hinton agar plates (MBA), Sterile 96-well polypropylene microtiter plates, and Sterile polypropylene microcentrifuge tubes. The test organisms included *Pseudomonas aeruginosa* (ATCC 9027), and *S. aureus* (ATCC 6538).

Five ml of MHB tubes are innoculated with test strains from MHA plates and are grown overnight at 37° C. on a shaker (180 rpm). The overnight culture of the test organism is diluted in MHB to give between $2 \times 10^5$ and $7 \times 10^5$ CFU/ml. Polypropylene microcentrifuge tubes are used to dilute the stock of indolicidin (e.g., L-IND) (10 mg/ml) 10-fold in sterile water at a concentration 10 times the required test concentration and for subsequent 2-fold sequential dilutions.

To obtain the high dose level of 100 $\mu$g/ml (=10 $\mu$g L-IND in a final volume of 100 $\mu$l), 10 $\mu$l of the stock of indolicidin is diluted in 90 $\mu$l of sterile water. The test article is serially diluted in a 2-fold fashion by transferring 50 $\mu$l of each dilution to 50 $\mu$l of sterile water to obtain concentrations of indolicidin in 10 $\mu$l aliquots of 50, 25, 12.5 and 6.25 $\mu$g/ml. Then, 100 $\mu$l of the bacterial suspension is dispensed in a predetermined number of wells in the polypropylene microtiter plate. Then 10 $\mu$l of the 10× test peptide dilutions is added to one well. Controls include one well for medium sterility and one well for bacteria alone. The microtiter plates are incubated at 37° C. for at least 24 hours and the wells are inspected visually for growth. The lowest dose that results in an absence of growth (absence of turbidity) is the MIC value.

C) Protocol # 3: Time-dependent Antimicrobial Activity Determination of L-IND at One Dose Level The objective of this protocol is to establish a procedure for determining the antimicrobial activity of indolicidin (e.g., L-IND) at 50 $\mu$g/ml over an extended exposure time up to 24 hours at room temperature. It is believed that this procedure more closely mimics the recommended use of lens-care products.

Exposure of the test organism to indolicidin occurs in a buffered solution for up to 24 hours with sampling for viability at different time intervals. Polypropylene 96-well microtiter plates and microcentrifuge tubes are used for exposure and dilution of indolicidin, respectively.

The following materials are used: sterile glass tubes containing 5 ml of Mueller-Hinton Broth (MHB), Mueller-Hinton agar plates, sterile 96-well polypropylene microtiter plates, and sterile polypropylene microcentrifuge tubes.

One or more of the following microorganisms are used in assays using this protocol or modification of this protocol: *Pseudomonas aeruginosa* (ATCC 9027), *Pseudomonas aeruginosa* (ATCC 27853), and *S. aureus* (ATCC 6538).

Five 5 ml of MHB tubes are innoculated with the tester strain(s) from MHA plates and grown overnight at 37° C. on a shaker (180 rpm). A micropipet tip is prewet for at least 2 minutes with 100 $\mu$l of the stock solution of indolicidin (e.g., L-IND). The test article is dispensed back in the stock solution vial and the pipette is reset to a volume of 10 $\mu$l. Polypropylene microcentrifuge tubes are used to dilute the stock of indolicidin (10 mg/ml) 10-fold in sterile water. To obtain a 10× solution of indolicidin with a dose level equivalent to 50 $\mu$g/ml dose level dilute 10 $\mu$l of the stock solution of indolicidin in 90 $\mu$l of sterile water. (The concentration of indolicidin in the final exposure volume of 100 $\mu$l will be 5 $\mu$g when 10 $\mu$l of the 10× solution is added to 100 $\mu$l of bacterial suspension). The overnight cultures are washed twice in sterile saline and resuspend in appropriate buffer. The washed culture is diluted in the appropriate buffer to give an estimated $10^6$ CFU/ml. Then 10 $\mu$l of the 10× test peptide dilutions are added to a predetermined number of wells in the polypropylene microtiter plate. 100 $\mu$l of the bacterial suspension is dispensed to the wells in the polypropylene microtiter plate containing the test chemical and mixed well. Controls include one well each for negative controls, i.e., bacteria only sampled at the initiation of the experiment and at the completion of the experiment. The microtiter plate is covered with aluminum foil to shield the exposure mixture from direct light and placed on the bench top at room temperature. At the end of each time interval, the mixture is diluted in an appropriate sterile buffer and plated for viable counts.

Survival is determined by counting the colonies appearing on plates after overnight incubation at 37° C. The results are expressed as CFU/ml and survival is expressed as the percent of the bacteria that survived the treatment.

D) Critical Micelle Test

In an aqueous solution of a surfactant, the surfactant is molecularly dispersed at low concentrations. At higher concentrations, however, when a certain critical concentration is reached, the molecules form micelles. These micelles are in equilibrium with the free surfactant molecules. The concentration that must be reached in order that micelles are formed is called the critical micelle concentration. Adequate cleaning effectiveness of a daily cleaner can be demonstrated in vitro by determining that the concentration of a surfactant (or surfactants) in a daily cleaner are higher than the critical micelle concentration of surfactant (or surfactants).

Many physical properties of the surfactant solution when plotted against the concentration show more or less sudden changes at the critical micelle concentration. By measuring such properties as electrical conductivity, interfacial tension, surface tension, refractive index, viscosity and light scattering as a function of the concentration of the surfactant, the critical micelle concentration is determined as the concentration at which the property versus concentration curve shows a change in slope. The hydrophobic part of the surfactant molecule is situated at the inside of the micelle, the hydrophilic part at the outside. Inside the micelles lipophilic substances may be solubilized.

The purpose of a daily cleaner is to remove loosely held lens deposits on the lens surface. Generally, a daily cleaner contains at least a surfactant which lowers surface tension of the solution to facilitate removal of loosely held lens deposits on the lens surface in conjunction with mechanical means (e.g., fingers). The concentration of a surfactant (or surfactants) in a daily cleaner should be sufficient enough to be higher than the critical micelles concentration of surfactant (or surfactants). The critical micelle concentration of surfactant may be significantly affected by pH, tonicity, and other inactive ingredients in the daily cleaner.

The following simple method of measuring surface tension of the surfactant (or surfactants) in a device medium can be used to determine the critical micelle concentration.

1. Solution 1: Prepare the daily cleaner medium (i.e., the daily cleaner without surfactants).
2. Solution 2: Prepare a reasonable concentration of the surfactant system (if more than one surfactant is in the daily cleaner the weight or mole ratio of the surfactant system should be the same as the one in the daily cleaner).
3. Solution 3: Prepare varying concentrations of the surfactant system in the daily cleaner medium by diluting Solution 2 with Solution 1.
4. Measure surface tensions of Solution 3 using a tensiometer.
5. Plot surface tension versus log concentration of surfactant system in the daily cleaner medium(Solution 3) and perform a least square linear regression to determine the critical micelle concentration.

E) Testing Antimicrobial Activity of Antimicrobial Peptides

The time course and dose-dependence of the antimicrobial activity of an antimicrobial peptide can be determined by incubating a microorganism with the antimicrobial peptide and determining the viability after various times of incubation or after treatment with various concentrations of the antimicrobial peptide.

Exemplary assays using indolicidin and indolicidin analogs were performed in 10 mM sodium phosphate buffer, pH 7.4, at 37° C., as described by Selsted et al. (1985) Infect. Immun. 45:150–154, which is incorporated herein by reference.

The dose response of a gram negative bacterial strain, Escherichia coli ML35, and a gram positive bacterial strain, Staphylococcus aureus 502A, to indolicidin was determined by incubating $2 \times 10^6$ colony forming units (CFU) of log phase bacteria with 0–25 µg/mL of indolicidin for two hours. Following incubation, the cultures were serially diluted and plated on nutrient agar. Viability of both gram negative and gram positive bacteria was reduced by at least four orders of magnitude in incubations containing 10 µg/mL of indolicidin. E. coli was more susceptible than S. aureus, as >95% of the input cells were killed after 2 hr incubation with 2.5 µg/mL indolicidin. The indolicidin diluent, 0.01% acetic acid, had no effect on either bacterial strain.

The kinetics of indolicidin antimicrobial activity was evaluated by incubating $2 \times 10^6$ E. coli with 25 µ/mL of indolicidin for 1 to 40 min. Following incubation for the appropriate time, an aliquot of the culture was removed and diluted and plated as described above. 25 µ/mL indolicidin reduced the number of E. coli CFU by three orders of magnitude within 5 min and the culture essentially was sterilized after 20 min.

The broad spectrum antimicrobial activity of indolicidin and indolicidin analogs also was determined using a gram negative bacterial strain, E. coli ML35, a gram positive bacterial strain, Staphylococcus aureus 502A, and a fungus, Cryptococcus neoformans, in an agar diffusion assay, essentially as described by Hultmark et al. (1983) EMBO J. 2:571–576 as modified by Lehrer et al. J. Immunol. Meth. 137:167–173. Briefly, nutrient-containing agar (or agarose) plates were seeded with a selected target microorganism and 5–10 mu/L of peptide was placed into a well formed in the solid medium or onto a disc placed on the surface of the medium. Following an appropriate incubation interval, microbial growth inhibition was visualized and quantitated by measuring the clear zone around each well or disc (see, Selsted, in Genetic Engineering, Vol. 15, pages 131–147, Plenum Press, NY, 1993).

F) Exemplary Formulations

Table 3 shows exemplary formulations based on 50 µ/ml of L-indolicidin.

TABLE 3

Exemplary formulations based on 50 µg/ml of L-indolicidin.

| Component | 1 | 2 | 3 | 4 |
|---|---|---|---|---|
| L-IND | 0.005 g | 0.005 g | 0.005 g | 0.005 g |
| Distilled H$_2$O | Dilute to 10 mL | Dilute to 10 mL | Dilute to 10 mL | Dilute to 10 mL |
| Sodium phosphate buffer | Dilute to 100 mL | Dilute to 100 mL | Dilute to 100 mL | Dilute to 100 mL |
| NaCl | | 8.7 g | 8.7 g | |
| Poloxamer | | | 0.25 g | 0.25 g |

L-indolicidin was purchased from Peninsula Laboratories, Inc., Belmont, Calif. SP is made by dissolving 2.747 g of disodium hydrogen phosphate in 250 mL of water and adding this to 0.7698 g of sodium dihydrogen phosphate monohydrate in 250 mL of water. Poloxamer is polyoxyethylene-polypropylene copolymer.

G) Determining the Effective Amount of Indolicidin in the Ophthalmic Solution

L-IND was received frozen in 3×2-mL glass screw-cap vials in 1-mL aliquotsat a stock concentration of 10 mg/mL in pyrogen-free saline. The material was stored frozen during the study. All tester strains (Table 4) were obtained from the American Type Culture Collection, Rockville, Md.

TABLE 4

Tester strains and growth media.

| Species and ATCC Number | Growth Medium |
|---|---|
| Pseudomonas aeruginosa 27853 | Nutrient broth and agar; Mueller-Hinton Broth and agar |
| Pseudomonas aeruginosa 9027 | Nutrient broth and agar; Mueller-Hinton Broth and agar |
| Staphylococcus aureus 6538 | Nutrient broth and agar; Mueller-Hinton Broth and agar |
| Escherichia coli 8739 | Trypticase Soy Broth and Agar |

Viable counts were determine by serial 10-fold dilutions and by plating on nutrient agar, trypticase soy agar of Mueller-Hinton agar plates. After overnight incubation at 37° C., colonies were counted and the results were expressed as colony-forming units per milliliter (CFU/mL). Survival of the treated bacteria was expressed as the % survival fraction compared to the L-IND non-treated control.

Actual number of colonies were enumerated for control and treated samples, which precluded any bias from influencing the results.

Example 2

Determination of the Minimal Inhibitory Concentration (MIC) of L-IND and Three Commercially Available Lens Care Products when Tested Against a Strain of *P. aeruginosa*

A) Experiment 1

The purpose of this experiment was to determine the minimal inhibitory concentration (MIC) of L-IND and three commercially available lens care products when tested against a strain of *P. aeruginosa* recommended by the Food and Drug Administration (FDA) for antimicrobial activity testing. Protocol 1 (Example 1) was used, but at a high dose range of between and 5,000 and 1.25 µg/ml with *P. aeruginosa* (ATCC 27853). The following test dosages were used (µg/ml):

1. L-IND at 5,000, 2,500, 1,250, 625, 312, 156, 78, 39, 20, 10, 5, 2.5 and 1.25 in PBS (phosphate buffered saline).
2. Softwear (CibaVision). Highest dose level was the undiluted product followed by 12 serial 2-fold dilutions in PBS solution.
3. Opti-Free (Alcon). Highest dose level was the undiluted product followed by 12 serial 2-fold dilution in phosphate buffered saline.
4. AOSept (American Optical). Highest dose level was the undiluted product followed by 12 serial 2-fold dilution in phosphate buffered saline.
5. Control commercial saline (Longs Drugs, Menlo Park, Calif.). Undiluted product only.

Phosphate buffered saline solution was used as a vehicle control and diluent the final incubation volume in glass test tubes was 1 ml, and the incubation time and temperature was one hour at 37° C.

A 100% survival was observed with the test organism *P. aeruginosa* at a cell density of $5.9 \times 10^5$ CFU/ml after exposure to all dose levels of L-IND. The peptide did not behave as predicted and may have been inactivated during the dilution and use process (it was later discovered that the presence of halide ions, e.g., Cl$^-$ inactivate the indolicidin). In contrast, there was no survival of *P. aeruginosa* at a cell density of $5.9 \times 10^5$ CFU/ml after exposure for one hour to AOSept up to the $10^{th}$ 2-fold dilution. Both the Opti-Free and Softwear lens-care solutions exhibited limited toxicity up to the $8^{th}$ 2-fold dilution.

The control vehicle, Longs Drugs Saline solution, tested at full strength exhibited no toxicity to the bacteria (data not shown). The viable counts obtained were $5.7 \times 10^5$ CFU/ml versus $5.9 \times 10^5$ CFU/ml for the negative control (bacteria in PBS).

B) Experiment 2

This experiment was a repeat of Experiment I with the following changes: An L-IND dose range between 100 µg/ml and 6.25 µg/ml was used to prevent aggregation and binding of L-IND during the diluting procedure at the high dose levels originally used. A 10 mM phosphate buffer, pH 7.4, was used instead of PBS. An additional bacterial strain, *S. aureus,* (ATCC 6538) a gram-positive bacterium, was used. The commercially available lens-care products Opti-Free, AOSept and Softwear, and the commercial saline control (Longs Saline) were omitted. Protocol 1 (Example 1) was used with the modifications described in experiment 1, above. Indolicidin (L-IND) was used at 100, 50, 25, 12.5 and 6.25 µg/ml, and 10 mM sodium phosphate buffer, pH 7.4, was used as a, vehicle control and diluent.

A 100% survival was observed with the test organism *P. aeruginosa* at a cell density of $2.01 \times 10^5$ CFU/ml after exposure to all dose levels of L-IND. In stark contrast to the results with Pseudomonas, there was no detectable survival of *S. aureus* exposed at a cell density of $4.1 \times 10^5$ CFU/ml to doses of 100, 50, 25 and 12.5 µ/ml of L-IND. At the lowest dose level tested, 6.25 µg/ml, there remained about a 3-log kill. Since the L-IND solution and protocol to test both species of bacteria were identical, there appeared a marked difference in susceptibility of the two organisms to the antimicrobial peptide solution used.

C) Experiment 3

This experiment was a repeat of Experiment 2 with the following changes: A different *P. aeruginosa* strain (ATCC 9027), prescribed in the FDA guidelines was included, and an *Escherichia coli* (ATCC 8739) strain was included to determine whether gram-negative organisms are more tolerant to L-IND compared to *S. aureus* (a representative Gram-positive bacterium). A cell density of at least 106 CFU/ml was used in antimicrobial activity testing procedures. Protocol 1 was used with the modifications described above. L-indolicidin was tested at concentrations of: 100, 50, 25, 12.5 and 6.25 µg/ml. 10 mM sodium phosphate buffer was used the vehicle diluent.

There was about a 4-log kill of *P. aeruginosa* 9027 at the 100 and 50 µg/ml dose level (compared to the control value of $3.2 \times 10^6$ CFU/ml). There was a gradual increase in survival with decreasing dose levels of L-IND, with a survival of 59% at the lowest dose level tested, namely 6.25 µg/ml.

The survival data obtained with *E. coli* 8739 indicated a 3-log kill between dose levels of 100 and 12.5 µg/ml and a 15% survival at the lowest dose level tested, namely 6.25 µg/ml. The cell density of the bacteria exposed to L-IND was $3.17 \times 10^6$.

There was no detectable survival of *S. aureus* exposed at a cell density of $4.1 \times 10^5$ CFU/ml to doses of 100, 50, 25 and 12.5 µg/ml of L-IND. At the lowest dose level tested, 6.25 µg/ml, there was about a 3-log kill.

Example 3

MIC Determination Using a Procedure Adapted for Evaluating Antimicrobial Peptides A) Experiment 4

The purpose of this experiment was to perform MIC determination using a procedure adapted for evaluating antimicrobial peptides (Example 1, protocol 2). Principal modifications include the use of polypropylene microtiter plates, polypropylene microcentrifuge tubes (for dilutions of L-IND) and the use overnight cultures of the test organisms inoculated in Mueller-Hinton broth (MHB) and appropriately diluted in MHB. Also water is used as the solvent and diluent for L-IND.

*P. aeruginosa* ATCC 9027 and *S. aureus* ATCC 6538 were used as the test organism and L-indolicidin was tested at concentrations of 100, 50, 25, 12.5 and 6.25 µg/ml. Sterile water was used as a solvent and diluent for L-IND and Mueller-Hinton broth was used as a growth medium for MIC determination. The final incubation volume polypropylene microtiter plates was 110 µl and the incubation was overnight (~18 hr) at 37° C.

The microtiter plates were inspected for growth after the overnight incubation. Growth as measured by visual inspection of the wells for turbidity was observed at all dose levels of L-IND tested with *P. aeruginosa*. Thus, no MIC value was obtained at the highest dose level tested, namely 100 μg/ml. A MIC value of 12.5 μg/ml was obtained for *S. aureus*.

B) Experiment 5

The purpose of this experiment was to perform an antimicrobial activity experiment in a time-dependent fashion in 10 mM sodium phosphate buffer at one dose level of L-IND, namely, 50 μg/ml, using polypropylene 96-well microtiter plates and polypropylene microcentrifuge tubes for preparation of the test article. This procedure was believed to more closely mimic the actual conditions the peptide will be subjected to in a commercial lens care product. Prior to exposure, the cells were washed 2 times in 10 mM sodium phosphate buffer, pH 7.4 to remove excess rich growth medium that may be adsorbing or inactivating the peptide.

Protocol 3 (Example 1) was used with *S. aureus* ATCC 6538 as the test organism. L-indolicidin was tested at 50 μg/ml only. Sterile water was used as a solvent for L-IND. 10 mM sodium phosphate buffer, pH 7.4 was used as a vehicle for exposure of bacteria to L-IND. The final incubation volume in polypropylene microtiter plates was 110 μl and the incubation times and temperature were 0, 1, 2, 5 and 15 minutes, at room temperature (temperature selected to more closely approximate consumer use conditions, compared to 37° C.).

Survival was determined by removing aliquots at the indicated times, diluting and plating on Mueller-Hinton agar plates. After overnight incubation at 37° C., colonies were counted. Results were expressed as CFU/ml and survival as % of the surviving fraction compared to the control (bacteria only) which was $3 \times 10^5$ CFU/ml.

There was no survival of *S. aureus* at any of the time points tested (i.e., 100% killed under the conditions used), even after only a 1-min exposure to the peptide solution.

C) Experiment 6

The purpose of this experiment was to repeat Experiment 4 under identical conditions using *P. aeruginosa* 9027, with the exception of one additional time point of 60 minutes. The culture was washed 2 times in 10 mM sodium phosphate buffer, pH 7.4.

Protocol 3 was used with the modifications described above. The test organism was *P. aeruginosa* 9027. L-indolicidin was tested at 50 μg/ml only. Sterile water was used as a solvent for L-IND. 10 mM sodium phosphate buffer, pH 7.4 was used as a vehicle for exposure of bacteria to L-IND. Final incubation volume in polypropylene microtiter plates was 110 μl, and incubation times were 0, 1, 2, 5 and 15 and 60 minutes at room temperature.

There was 100% survival after exposure of Pseudomonas to 50 μg/ml of L-IND for 1, 2 and 5 minutes. However, after 15 minutes, survival was reduced to 19% compared to the control and after 60 min survival had been reduced by about a 2-logs. It should be noted that an overnight culture of *P. aeruginosa* was used that had remained at room temperature for an additional 24 hours instead of the standard overnight culture (18 hour culture).

D) Experiment 7

This experiment was a repeat of Experiment 6 using the same exposure protocol, but with a prolonged exposure time, namely 24 hours, and using washed cells of an 18-hour old overnight culture of *P. aeruginosa* inoculated in Mueller-Hinton broth. Incubation times were 0 and 24 hours, at room temperature.

There was no apparent survival (100% killed) after 24 hours of exposure to 50 μg/ml of L-IND. However, there were no plate counts from the undiluted exposed bacteria as the full 100 μl volume exposure mixture was used for the 10-fold dilutions.

E) Experiment 8

This experiment was a repeat of Experiment 7 using the same exposure conditions, but with more frequent time intervals extending over a total period of 24 hours. Furthermore, test two strains of *P. aeruginosa* were used to assess strain-to-strain variability. Final volume in each well of the 96-well polypropylene microtiter plate was increased to 220 μl (up from 110 μl to allow additional sampling). The increased volume allowed agar plating of 0.1 ml of the undiluted exposure mixture to establish a viable count.

Protocol 3 was used with the modifications described above. The test organisms were *P. aeruginosa* 9027 and *P. aeruginosa* 27853. L-indolicidin was tested at 50 μg/ml only. Sterile water was used as the solvent for L-IND. 100 mM sodium phosphate buffer, pH 7.4 (instead of 10 mM) was used as the vehicle for exposure of bacteria to L-IND. The final incubation volume in polypropylene microtiter plates was 220 μl and incubation times and temperature were 0, 1, 2, 4, 6, 8, 13 and 24 hours, at room temperature.

There was no survival at any of the time points sampled with either of the *P. aeruginosa* strains tested. The control (bacteria only) incubated for up to 24 hours in the 100 mM sodium phosphate buffer showed a 100% survival, showing their ability to tolerate a ten-fold higher buffer strength, as shown below in Table 5.

TABLE 5

Bacterial growth.

| *P. aeruginosa* Strain No. | Incubation Time (hr) | Growth Buffer Only (CFU/ml) | Buffer and L-indolicidin 50 μg/ml |
|---|---|---|---|
| ATCC 27853 | 0 | $9.0 \times 10^5$ | 0 |
|  | 24 | $9.6 \times 10^5$ | 0 |
| ATCC 9027 | 0 | $5.0 \times 10^5$ | 0 |
|  | 24 | $5.4 \times 10^5$ | 0 |

F) Experiment 9

The purpose of this experiment was to repeat Experiment 8 under identical conditions with the 100 mM sodium phosphate buffer but with exposures at more frequent time intervals, extending over a total period of 1 hour to determine more precisely at which time interval cell killing, is initiated. Protocol 3 was used with the modifications described above. The test organisms were *P. aeruginosa* 9027 and *P. aeruginosa* 27853. L-indolicidin was tested at 50 μg/ml only. Sterile water was used as the solvent for L-IND. 100 mM sodium phosphate buffer, pH 7.4 was used as the vehicle for exposure of bacteria to L-IND. The final incubation volume was 220 μl. Incubation times and temperature were 0, 1, 2, 5, 15 min and 1 hour, at room temperature.

After exposures of 1 and 2 minutes, the viability of *P. aeruginosa* (ATCC 9027) was down by about 1-log. After 5 minutes, there were only 34 colonies on the plate that had been seeded with 0.1 ml of the undiluted exposure mixture. No colonies were observed on any of the plates seeded with bacteria exposed to L-IND for 15 and 60 minutes. Similar results were obtained with *P. aeruginosa* (ATCC 27853), indicating that exposures of between 15 and 60 min duration can induce virtually complete killing of even the more antibiotic tolerant Pseudomonas strain (ATCC 27853).

G) Experiment 10

This experiment used a 10 mM sodium phosphate buffer with the two *P. aeruginosa* strains with sampling at several time intervals over a total exposure period of 24 hours, to determine whether the results obtained in Experiment 8 with 100 mM sodium phosphate buffer are reproducible at 10-fold lower concentrations of buffer salts.

Protocol 3 was used with the modifications described above. P. aeruginosa 9027 and P. aeruginosa 27853 were the test organisms. L-indolicidin was tested at 50 μ/ml only. Sterile water was used as the solvent for L-IND. 10 mM sodium phosphate buffer, pH 7.4 was used as the vehicle for exposure of bacteria to L-IND. Final incubation volume was 220 μl, and incubation times and temperature were 0, 1, 2, 4, 8 and 24 hours, at room temperature.

With an initial cell density of $2.0 \times 10^6$ CFU/ml obtained with both strains (control value=bacteria only), there was close to a 6-log cell reduction with both strains of P. aeruginosa as early as after 1 minute exposure to 50 μg/ml of L-IND. The viable count of the bacterial suspension after 24 hours of incubation in the polypropylene microtiter plate at room temperature was the same as the control value, namely $2.3 \times 10^6$ for P. aeruginosa (ATCC 9027) and $2.1 \times 10^6$ for P. aeruginosa (ATCC 27853), demonstrating a high net kill effect in the treated suspensions.

H) Experiment 11

The purpose of this experiment was to determine the viability of two Pseudomonas strains after exposure up to 15 minutes to L-IND (50 μg/ml) in 10 mM sodium phosphate buffer, pH 7.4. Since high killing was observed in experiment 10 in multi-hr exposures to L-IND, this current experiment was designed to dissect how quickly Gram negative bacteria can be killed.

Protocol 3 was used with P. aeruginosa (ATCC 9027) and P. aeruginosa (ATCC 27853). L-indolicidin was used at 50 μ/ml only. Sterile water was used as the solvent for L-IND. 10 mM sodium phosphate buffer, pH 7.4 was used as the vehicle for exposure of bacteria to L-IND. Final incubation volume was 110 μl, and incubation time and temperatures were 0, 1, 2, 5 and 15 minutes, at room temperature There was a 100% survival observed with Pseudomonas strains after an exposure to L-IND (50 μg/ml) for up to 15 minutes in a 10 mM sodium phosphate buffer system (data not shown). It appears from this initial study that killing of Pseudomonas may not take place within 1 hr, but between 1 hr and a few hr of exposure to L-IND under the conditions described.

I) Experiment 12

This experiment was a repeat of Experiment 11 but with prolonged exposure times. Incubation times and temperature were 0, 1, 2, 4, 6, 12 and 24 hours, at room temperature.

TABLE 6

Survival of P. aeruginosa ATCC 9027 and ATCC 27853

| Exposure Time (hr) | P. aeruginosa (ATCC 9027) CFU/ml | P. aeruginosa (ATCC 27853) CFU/ml |
| --- | --- | --- |
| 0 | $1.2 \times 10^6$ | $2.4 \times 10^6$ |
| 1 | $6.5 \times 10^5$ | $1.6 \times 10^6$ |
| 2 | $1.1 \times 10^4$ | $1.1 \times 10^5$ |
| 4 | 0 | 0 |
| 6 | 0 | 0 |
| 12 | 0 | 0 |

The results are illustrated in Table 6. Both strains did survive exposure to L-IND (50 μ/ml) for up to 2 hours. After 4 hours exposure, however, there was no detectable survival. The viable count in the control sample (24 hours in 10 mM sodium phosphate buffer) was $1.2 \times 10^6$ CFU/ml for P. aeruginosa (ATCC 9027) and $2.4 \times 10^6$ CFU/ml for P. aeruginosa (ATCC 27853), indicating a high net killing by L-IND after 2 hr of exposure of the treated bacterial suspensions.

Example 4

Antibacterial Activity of L-IND in 6 Different Carrier Systems

The purpose of this experiment is to perform an antimicrobial experiment with 50 μg/ml L-IND in six different carrier systems that are compatible with existing lens-care products. The test organisms were S. aureus (ATCC 6538) with exposure times of 0, 1, 2, 5 and 15 minutes, and two P. aeruginosa strains (ATCC 27853 and 9027) with exposure times of 0, 1, 2, 4, 6 and 24 hours at room temperature.

Sterile water was used as the solvent for L-IND. The following six vehicles were used for exposure of bacteria to L-IND: 1) 0.85% sodium chloride prepared in water; 2) 0.85% sodium chloride prepared in 10 mM sodium phosphate buffer, pH 7.4; 3) 2% boric acid prepared in 10 mM sodium phosphate buffer, pH 7.4; 4) 0.85 % sodium chloride and 2% boric acid prepared in 10 mM sodium phosphate buffer, pH 7.4; 5) Longs Non-Preserved Saline Solution; and 6) 10 mM sodium phosphate buffer, pH 7.4. The final incubation volume was 110 μl. Incubation times and temperature were as indicated above The 5 ml of the overnight cultures were washed twice in sterile saline. The pellet was resuspended in 1 ml of sterile saline. Aliquots of 0.1 ml of the concentrated cell suspension was diluted 10-fold in the appropriate vehicle carrier systems and further diluted in each of the appropriate vehicle carrier systems to get a final cell density of about $10^6$ CFU/ml. Aliquots of 100 μl of each of the 6 cell suspensions were then delivered to the wells of the polypropylene microtiter plate.

Phosphate buffer by itself was found to be a highly compatible carrier for L-IND, consistently yielding the most reliable results. Variable and inconsistent results were obtained with the other vehicle carrier systems.

Example 5

Testing Corneal Penetration of a Radioactive Topical Ocular Indolicidin Formulation in Male Rabbits The objective of this study was to determine the corneal penetration potential of a $^3$H-labelled indolicidin molecule. The $^3$H labeled L-indolicidin; L-IND was tested for corneal penetration using New Zealand White Rabbits (Western Oregon Rabbit Co.). The rabbit is one of the model species for the assessment of toxicity and is one of the species recommended for that purpose by toxicity testing guidelines of all regulatory agencies. See "Animal Models in the Evaluation of Chemotherapy of Ocular Infections" in Experimental Models in Antimicrobial Chemotherapy, Vol 1, p 187–211.

Administration of $^3$H-L-IND was by epicorneal application into both eyes, 20 μL L-IND once hourly for six applications. The animals were euthanized immediately prior to harvesting of aqueous humor.

This study was not performed in accordance with the U.S. FDA "Good Laboratory Practice for Nonclinical Laboratory Studies," as described in 21 CFR Part 58. All operations pertaining to this study, unless specifically defined in this protocol, were performed according to the standard operating procedures of the laboratory and any deviations were documented.

Male animals were initiated as young adults and weighed 2–3 kg. Two animals were assigned to the test (2/group; one treatment group). General procedures for animal care and housing were in accordance with NRC Guide for the Care and Use of Laboratory Animals (1996) and the U.S. Department of Agriculture through the Animal Welfare Act (7 U.S.C. 2131), 1985 and Animal Welfare Standards incorporated in 9 CFR Part 3, 1991. No contaminants were to be present in the food, water, or bedding which could interfere and affect the results of the study. Copies of appropriate feed and water analysis reports are included in the study record.

Clinical signs were evaluated immediately after $1^{st}$ dose administration and immediately prior to euthanasia and necroscopy. Necroscopy was performed on day 1. Euthanasia was by an overdose of intravenous sodium pentobarbital.

Evaluations were confined to the eye. As much aqueous humor fluid was harvested as possible and fluid was pooled from both eyes as appropriate. The corneal surface of each eye was liberally flushed with saline and blotted dry prior to collection in order to prevent any contamination from the corneal surface to the aqueous humor. An estimate of the total volume of aqueous humor harvested was recorded and analyzed for $^3H$ content. Approximately 150 μL was collected from each eye.

The two samples of aqueous humor from each of the rabbits were analyzed for their radioactivity levels. The analysis was performed in a Mark III liquid scintillation counter (TM Analytic Inc., Elk Grove Village, Ill.). Before counting, the samples were combusted in a Packards' Model 307 (Packard Instrument Co.). The overall counting efficiency of tritium was 33.5%.

The aqueous humor samples were counted in duplicate (0.1 5 mL each for rabbit #1 and 0.2 mL each for rabbit #2). The radioactivity level in these samples was equal to that of background counts thereby showing no net counts in the samples.

Analysis of the solution used, (1 mg in 0.67 mL) for dosing showed that the radioactivity level in it was approximately one-third of that expected (stated radioactivity: 3.67 μCi in 1 mg; radioactivity found: 1.03 μCi). Nonetheless, 22,780 counts per minute (cpm) of radioactivity in 20 μL was applied six times to each eye; yet the counts in ~0.2 mL of aqueous humor were between 50 to 92 cpm against a background of 60 to 75 cpm. Thus, it appears $^3H$-Indolicidin did not penetrate the cornea.

Example 6

Testing the Toxicity of Indolicidin Formulations in Male and Female Mice and Male Rabbits The objective of this study was to determine if the treatment regimen proposed for the efficacy study of the defensin formulations caused target organ toxicity. This study is not intended to support application for research or marketing permits for products regulated by governmental agencies. The purpose of this study is to provide range-finding data is therefore, not within the scope of Good Laboratory Practice Guidelines.

The experimental design is illustrated below in Table 7.

TABLE 7

Experimental design for toxicity study.

| Species | Route of Administration | Sex | Dose Group (μg/mL peptide) | No. of Animals per Dose Group |
|---|---|---|---|---|
| Mice | intravaginal | F | 10, 100, 1000 | 2 |
| Mice | intraperitoneal | M | 10, 100, 1000 | 2 |
| Rabbits | topical ocular | M | 10, 100, 1000 | 2 |

*For all test articles except BNP-A-amide which will be evaluated at 30, 300, and 300 μg/mL.

Mice were treated by intravaginal administration twice daily at ~12 hour intervals administered on Days 1 through 4. Mice were treated intraperitoneally three times on Day 1 at ~4 hour intervals, and twice daily at ~12 hour intervals administered on days 2 through 4.

Rabbits were treated four times on Day 1 at ~1 hour intervals, and twice daily at ~12 hour intervals administered on Days 2 through 4.

Dosing volumes were 0.1 mL/mouse (intravaginal), 0.1 mL/mouse (intraperitoneal), and 20 μL/rabbit. The study lasted 5 days, with day 1 the first day of dose administration.

The animals were treated with L-indolicidin (test code All-L-IND), D-indolicidin (test code All-D-IND), All-Phe-indolicidin (test code All-L-Phe-IND), or BNP-A-amide (test code All-L-BNP-A-amide). The dose formulations were supplied in pyrogen-free saline.

In the intravaginal study in mice, no deaths occurred with the four test articles and one animal in the 10 μg/mL D-indolicidin dose group showed a clinical sign of alopecia on Day 1 (first dose administration) through to the end of the study.

There were two deaths in the intraperitoneal study in mice: one in the 100 μg/mL D-indolicidin dose group and the other in the 100 μg/mL All-Phe-indolicidin dose group. The D-indolicidin animal showed adverse clinical signs of hunched posture and ruffled fur (Day 1; third dose administration), and hypoactivity (Day 3; seventh dose administration) until its death on Day 4 (eighth dose administration). The animal dosed with All-Phe-indolicidin did not show any adverse clinical signs up to its death on Day 3 (fifth dose administration). The only other test article-related adverse clinical sign was ruffled fur in the 1000 μg/mL All-Phe-indolicidin dose group observed on Day 2 (fourth dose administration). Clinical signs due to animals fighting were noted in several dose groups.

No deaths and no test article-related clinical observations were noted with any of the four test articles in the ocular study in rabbits. One animal in the 30 μg/mL BNP-A-amide dose group had a discoloration of the right eye following each dose administration on Day 1; however, the eye returned to normal by the fifth administration on Day 2. This observation is most likely due to repeated manipulation of the eye and not test article induced. Two animals had diarrhea and stained fur, which is likely due to Coccidia exposure prior to the start of the study.

Tissues from the reproductive tract (ovaries, oviducts, uterus, cervix, vagina, vulva) of mice treated intravaginal with a dose of 0.1 mL/mouse L-indolicidin, D-indolicidin or All-Phe-indolicidin at 10, 100 or 1000 μg/mL or BPN-A-amide at 30, 300 or 300 μ/mL were within normal limits.

There were no gross alternations in mice treated intraperitoneally with a dose of 0.1 mL/mouse L-indolicidin, D-indolicidin or All-Phe-indolicidin at 10, 100 or 1000

μg/mL or BPN-A-amide at 30, 300 or 3000 μg/mL, and no tissues were preserved for microscopic evaluation.

The rabbit eyes were all histologically normal. No toxic changes were produced by topical ocular instillation of a dose of 20 μ L/rabbit L-indolicidin, D-indolicidin or All-Phe-indolicidin at 10, 100 or 1000 μg/mL or BPN-A-amide at 30, 300 or 3000 μ/mL.

No deaths or biologically significant clinical signs of toxicity were observed with L-indolicidin, D-indolicidin or All-Phe-indolicidin at 10, 100 or 1000 μg/mL or BPN-A-amide at 30, 300 or 3000 μg/mL when administered intravaginal or by topical ocular instillation. In the intraperitoneal study, no deaths or biologically significant clinical signs of toxicity were observed with L-indolicidin at 10, 100 or 1000 μg/mL; D-indolicidin at 10 or 1000 μ/mL; All-Phe-indolicidin at 10 μg/mL; or BPN-A-amide at 30, 300 or 3000 μg/mL.

Example 7

Testing the Storage Life of Formulations in Accordance with the Invention

The objective of this task was the development of a convenient way to quantitate the concentration of indolicidin solutions.

A) Assay #1. Solubility of L-IND in 0.01% Acetic Acid 4.97 mg of L-IND #036752, stored at 4° C. in a desiccation) was weighed into a polypropylene microfuge and dissolved in 0.01% acetic acid. The dry powder went into solution immediately, yielding a clear and colorless solution.

B) Assay #2. Quantitation of L-IND using the BCA Protein Assay

The Pierce (Rockford, Ill.) BCA Protein Assay is based on the colorimetric change which occurs when Bicinchonicic acid bind to cysteine, cystine, tryptophan, and tyrosine. The assay performed by incubating the protein with reagents provided in the kit for 30 min. The absorbance measured between 590 and 650 nm using a plate reader is proportional concentration of protein in the solution being measured.

Serial 1:2 dilutions of L-IND were made in phosphate buffered saline (PBS) or 0.01% acetic acid. The peptide dilutions were incubated with assay reagents for 30 min at 37° C. The absorbance was measured between 590 and 650 nm using 96-well polystyrene microtiter plates. Although the peptide reacted with the BCA reagents in the same manner in both acetic acid and PBS, the curve was linear only at high concentrations of peptide (i.e., 2–10 mg/ml). The working range of indolicidin is significantly lower than 2 mg/ml, so another method of determination of peptide concentration had to be investigated.

C) Assay #3. Behavior of L-IND During $OD_{280}$ Measurement

L-IND was diluted to 100 μg/ml in either 0.01% acetic acid or PBS. Absorbance readings in a spectrophotometer were taken at intervals for over 30 min using glass (quartz) cuvettes. L-IND in PBS gave constant readings for the entire time period, whereas the absorbance of L-IND in acetic acid started very low and increased until it almost reached the PBS reading at 35 minutes.

D) Assay #4. Development of a Calibration Curve for the Determination of the Concentration of L-IND in PBS.

Two glass (quartz) cuvettes containing 1 ml PBS were blanked at $OD_{280}$ in the spectrophotometer. One μl of a 10 mg/ml stock of L-IND was added to the PBS, mixed, and a reading taken. This was repeated until a total of 20 μl had been added. The curve generated was linear up to 170 μg/ml.

E) Method for the Quantitation of L-Indolicidin

The concentration of L-IND in sample solutions diluted in PBS can be determined by measuring their absorbance at 280 nm. The concentration can be calculated using the equation:

$$(OD_{280} - 0.0027)/0.0122 = \mu g/ml \text{ L-Indolicidin in solution}$$

This assay is valid for L-IND concentrations between 10 μg/ml and 170 μg/ml.

Example 8

Determination of Compatibility of L-Indolicidin Solutions when Stored in a Commercially Available Plastic Container-Preliminary Study The objective of this study was to determine if there is significant and rapid binding of L-IND to a typical plastic bottle such as the type to be used to store, ship and use the lens-care solution. The 2-week study reported here was a range-finding task to determine if there was substantial binding and incompatibility, and its results helped plan a more extensive stability study over a period of 8 months.

The two commercial containers were used that previously contained the commercial product RENU®, a multi-purpose solution for all soft contact lenses not requiring enzymatic cleaning, and manufactured by Bausch & Lomb. These containers hold a volume of 89 ml and came with a dispenser that precludes the removal of the cap, which aids in keeping the solution sterile. The lot number of the RENU® lens-care solutions used was GE7089, having an expiration date of May 1999.

The containers were prepared for the L-IND stability study by discarding the RENU® lens care solution, and by rinsing, 3 times with either sterile 10 mM sodium phosphate buffer (SP), pH 7.4 or 10 mM SP supplemented with 0.85 % (w/v) sodium chloride (SP+NaCl).

The test article, L-IND peptide solution, was prepared fresh from dry L-IND powder (Lot #036752). Two solutions were prepared for evaluation, to a final concentration of 50 μg/ml in 50 ml of 10 mM SP and 10 mM SP+NaCl. For this purpose a stock solution was prepared by weighing out 5 mg of L-IND and dissolving it in 10 ml of 0.01% acetic acid in a pyrogen free sterile Teflon container. A 10-fold dilution of this stock was then made by transferring 5 ml of the stock solution to each of the containers to which was then added 45 ml of either 10 mM SP or 10 mM SP+NaCl. After mixing by slowly shaking, the solutions were maintained at room temperature for the duration of the study.

It should be noted that the 5 ml of the L-IND stock solution was added to the empty containers. This was followed by addition of 45 ml of the respective buffer systems. The addition of peptide concentrate to the empty containers would enhance binding of the peptide to the plastic. Had excessive binding resulted, a less stringent procedure of adding the peptide concentrate to bottles pre-filled with buffer would have been adopted in subsequent experiments.

The stability of L-IND in each container was determined at times 0 h, 24 h, 48 h, 72 h, 7 d, 10 d and 14 d. At each sampling point, the contents of each of the two containers was shaken gently 3 times in a back and forth rocking motion. Three aliquots of about 1.5 ml of the solutions containing L-IND were removed. One aliquot was used immediately for determining the stability of L-IND by exposure to *Staphylococcus aureus* (see below). The other aliquots were stored in the freezer (−20° C.). One of these aliquots was kept until the end of the monitoring period, which was 14 days. At that time all the frozen samples were thawed and tested for stability of L-IND by bioassay.

*Staphylococcus aureus* (ATCC 6538) obtained directly from the American Type Culture Collection was the test organism. The bacterium was grown overnight at 37° C. in 5 ml of Mueller-Hinton (MH) broth on a shaking platform (180 rpm). The overnight culture was washed 2 times in sterile saline by centrifugation at 7,000 RPM. One half of the cells were then resuspended in 2.5 ml of sterile 10 mM SP, while the other half was resuspended in 2.5 ml of 10 mM SP+NaCl. Each washed culture was then diluted to give an estimated $10^7$ colony-forming-units (CFU) per 20 µL.

*S. aureus* was exposed at room temperature to each of the samples, removed at the different time points, for 0, 15 and 60 minutes, and for 4 hours. For this purpose 0.25 ml of each L-IND solution was dispensed into wells of a 96-well polypropylene titer plate. A volume of 20 µl of the 10× washed bacterial suspension was then added to each well. The estimated cell density thus obtained per well was about $10^6$ CFU/ml. An additional control was included in each experiment, namely 10 mM SP and 10 mM SP+NaCl with bacteria only maintained in a well for the duration of the exposure (4 hours). This control was included to determine if the buffer systems alone, independent of L-IND, would have an effect on the viability of *S. aureus*.

After the indicated exposure time, 0.1 ml aliquot of the mixture in each well was transferred to 0.9 ml of sterile saline (10-fold dilution). Three additional 10-fold dilutions were then made by addition of 0.2 ml aliquots to 1.8 ml of sterile saline. Aliquots of 0.1 ml of each dilution were then plated in duplicate on Mueller-Hinton agar (MHA) plates. An aliquot of 0.1 ml of the undiluted exposure mixture was also be plated (0 dilution). A sterile glass spreader was used to evenly distribute the cells over the surface of the agar. The plates were incubated overnight at 37° C. Colonies were counted and the results were tabulated as CFU/ml.

At the end of the stability monitoring period (14 days), all samples that were kept frozen were thawed. The stability of L-IND was determined in these samples on the same day using the same procedure for determining its stability immediately after each sampling time.

Actual number of colonies were enumerated for control and treated samples, which precluded any bias from influencing the results.

There were two variables in the determination of L-IND stability in this study. First, was the difference in the buffering systems, one consisting of 10 mM SP, the other of 10 mM SP supplemented with 0.85% sodium chloride. Second, the potential difference in the relative efficacy L-IND after freezing and storage for different times up to 14 days.

The results obtained in the initial testing of L-IND prepared in 10 mM SP, show about a 3-log kill of *S. aureus* within 15 minutes exposure on each test day. A similar killing effect was observed after 60 minutes exposure. Survival decreased to between 4 and 5 logs after 4 hours of exposure.

Overall, there was a reasonable amount of variability in the results obtained on the different test days, but it must be kept in mind that each assay was a completely independent experiment and some variability was anticipated. The results obtained with the negative control sample (bacteria only) maintained for 4 hr in the 96-multiwell plate indicate that the reduced survival of the bacteria to L-IND was solely due L-IND in the solution.

The data obtained with the second buffer system (10 mM SP+NaCl) during the initial 14 day testing period showed a slight dose-related decrease in survival between 0 h and 60 minutes exposure with about a 50% kill and, at best, a 2-log kill after 4 hours of exposure. There was a fair amount of scatter at all time points.

The results obtained with the frozen samples in 10 mM SP confirmed the effectiveness of L-IND in this buffer system as an antimicrobial agent. There was between a 4- and 5-log kill of *S. aureus* after 15 minutes of exposure and by 60 minutes of incubation, there was 100% kill As in the initial experiments, the 4-hr negative control (buffer only) sample revealed that the survival of the bacteria remained at 100%.

The results obtained with the frozen samples in 10 m 1 SP+NaCl show that the antimicrobial activity of L-IND remains essentially the same as that observed in the initial experiment, namely a dose-related kill of only about 2 logs after 4 hours of exposure.

Data comparisons highlight important conclusions from the different experiments. First, the results indicate that any killing effect was due to the presence of L-IND in the two buffering systems. Second, the effectiveness of L-IND in 10 mM SP was higher than in the buffering system consisting of 10 mM SP+NaCl. Thus the reduced activity of L-IND in the latter buffer is attributed to the presence of NaCl. The addition of sodium chloride to a phosphate buffer base solution does not help and often reduces the antimicrobial activity of L-IND.

Third, the results indicate that freezing the L-IND samples prior to quantitation appear to enhance the antimicrobial activity of L-IND, the 10 mM SP buffer. Also, it appears that there was less variability in the survival of *S. aureus* when the frozen samples are tested. However, it should be noted that all the frozen samples were tested on the same day, within a single experiment, where less variability is expected. Fourth, the antimicrobial activity of L-IND at 50 µ/ml appears to be stable over a period of 14 days whether formulated in 10 mM SP or 10 mM SP+NaCl. There was no obvious or dramatic adsorption of the active agent to the plastic container.

A statistical analysis of the results indicated that there was no statistical difference in the data obtained at the different exposure times with any of the L-IND solutions under the different conditions used in these studies, namely frozen and non-frozen L-IND in 10 mM SP and frozen and non-frozen L-IND in 10 mM SP+NaCl.

Example 9

Confirmation of Antibacterial Activity of L-IND Solutions

The purpose of this study was a confirmation of results previously obtained with new L-IND solutions, using Gram negative (*P. aeruginosa* ATCC 9027) and Gram positive (*S. aureus* ATCC 6538) tester strains of bacteria specified by the FDA. The following test substances were used: 1) L-IND at 50 µg/ml in 10 mM phosphate buffer, pH 7.4; and 2) AOSept (American Optical) undiluted commercial product (3% hydrogen peroxide as the major active ingredient).

Phosphate buffered solution (10 mM sodium phosphate) was used as the vehicle control and diluent. Incubation times and temperature were as indicated (1–5 min), at room temperature (23° C.).

Initial concentration of 2×10⁶ CFU/ml for Pseudomonas and 1×10⁶ CFU/ml for Staphylococcus were used.

The results indicate that L-IND can perform reliably as an antibacterial. 6 log reductions in CFU were achieved.

Example 10

MIC Assays Conducted With Reference to the FDA Premarket Notification (510(K)) Guidance Document for Contact Lens Care Products: Micro Appendix B Disinfection Efficacy Testing—Part 1. Stand-Alone Procedure for Disinfecting Products and Part 2. Regimen Procedure for Disinfecting Regimens Test organisms were prepared by thawing frozen stock culture and placing the culture (0.1–1 ml) into growth medium (~50 ml). The culture was incubated at the appropriate temperature overnight (~16–20 hr) with shaking (150–180 rpm). Then 10 to 50 ml of the overnight culture was spun down (7,500 rpm, 6–10 min at 4° C.) the spent medium discarded. The culture was washed by resuspending the cell pellet in equal volume of NaCl, 1 mM sodium phosphate buffer, or 10 mM sodium phosphate buffer and spinning again at 7,500 rpm. The supernatant was discarded and the wash repeated.

The cell pellet was resuspended in the appropriate experimental buffer solution (1 to 10 mM sodium phosphate buffer). The suspension was diluted to a 10× concentrated stock cell density of 1 to 5×10⁷ CFU/ml.

Test organisms as provided in the FDA guidelines are listed in Table 8.

TABLE 8

Recommended test organisms.

| Organism | ATCC No. | Growth Medium | Temperature |
|---|---|---|---|
| Pseudomonas aeruginoosa | 9027 | Mueller-Hinton broth* | 35–37° C. |
| Staphylococcus aureus | 6538 | Mueller-Hinton broth | 35–37° C. |
| Serratia marcescens | 13880 | Mueller-Hinton broth | 20–25° C. |
| Candida albicans | 10231 | Sabouraud dextrose broth | 20–25° C. |
| Fusarium solani | 36031 | Potato dextrose broth/agar | 20–25° C. |
| Acanthamoeba divionensis | 50251 | ATCC PYG 712 medium | 25–27° C. |
| Acanthamoeba divionensis | 50253 | ATCC PYG 712 medium | 25–27° C. |

*Bacto Mueller-Hinton medium was developed for testing the susceptibility of microorganisms to antimicrobial agents and was therefore used in the MIC testing of L-IND.

A 5,000 µg/ml stock indolicidin (e.g., L-IND) solution was prepared in water by weighing out 5 mg and dissolving it in 1 ml water. The tube was inverted to dissolve the polypeptide. The stock was diluted 2-fold in water or sodium phosphate buffer to prepare 10× concentrated stock solutions: 2500, 1250, 625, 312, 160, 80, 40, 20, and 10 µg/ml or the stock was diluted 1:10 in water or sodium phosphate buffer followed by the 2-fold dilution series resulting in working concentration series (1×) of indolicidin. Solutions were used immediately or stored at −20° C.

MIC testing was performed in either 1.5 to 2 ml polypropylene tubes or 96-well polypropylene plates. To each tube or well was added the following: 160 µL buffer, 20 µl 10× concentrated indolicidin (e.g., L-IND) solution, and 20 µl 10× concentrated test organism OR 200–230 µl 1× concentrated indolicidin solution and 20 µl 10× concentrated test organism. The tubes were mixed by briefly vortexing and wells by pipetting up and down several times. Exposure was at room temperature 1 to 19 h (typically 4 hr for bacteria and 18 hr for fungi and yeast).

After exposure to indolicidin, the solution was serially diluted 10-fold in 0.85% saline to inactivate the indolicidin and was plated onto Mueller-Hinton agar (50 to 200 µl/plate).

The plates were incubated at the appropriate temperature for each test organism for 18 to 36 hr. Colonies were then counted the density/viability of the starting culture or inoculum was calculated. MIC was determined at the lowest concentration of indolicidin (e.g., L-IND) in which no growth is observed. Log kill may also be determined based on the viability (CFU/ml) of the controls without L-IND.

The results (MIC and Log kill from multiple experiments) are shown in Table 9.

TABLE 9

MIC and Log Kill for L-indolicidin.

| Organism | MIC µg/ml | Log Kill |
|---|---|---|
| P. aeruginosa | 16–64 | 4–6 |
| S. aureus | 216–125 | 4–6 |
| S. marcescens | 125–250 | 4 |
| C. albicans | 125–500 | 4 |
| F. solani | 62.5 | 5 |
| A. divionensis | 32 | 5–6 |

Example 11

Formulation of L-IND: Optimization of Buffer Concentration, Exposure Length, Additive Concentrations (Surfactants and Chelating Agents) with L-IND Concentrations at and Below MIC Levels The purpose of this experiment was to determine whether additives such as surfactants (pluronic) and chelating agents (EDTA) would effect L-IND activity. The concentrations selected for each organism tested ( S. aureus and P. aeruginosa) were based on the L-IND MIC for that organism. A lower concentration was also selected to determine whether the additives enhanced the antimicrobial activity of L-IND. Concentrations of L-IND ranged from 3.12 to 50 µg/ml. The concentration of sodium phosphate (SP) buffer was also examined and ranged from 1 to 10 mM.

A full factorial experimental design was used with 5 factors at 2 levels: 1) Exposure time (1 hr, 4hr); 2) SP buffer concentration, pH 7.4 (1 mM, 10 mM); 3) Surfactant concentration (0.25 wt %, 0.5 wt %); 4) EDTA concentration (0.1 wt %, 0.2 wt %); and 5) L-IND concentration (MIC and lower).

As described in the MIC procedure (Example 10), cultures were exposed to solutions containing various combinations of the above components for 1 or 4 hr at room temperature. Appropriate controls were conducted to evaluate the effects of individual components. Each replicate (assay done in triplicate) was then diluted 10-fold in NaCl and plated onto Mueller-Hinton agar. Colonies were then counted and log kill, effects of each additive, SP buffer concentration, and length of exposure on L-IND activity were examined.

The results of the matrix study with *S. aureus* show that the presence of pluronic and EDTA at either concentration in 1 mM SP buffer did not affect the activity of L-IND. No inhibition of activity was observed at 12.5 µg/ml L-IND (6-log kill; MIC of *S. aureus*) nor was any enhancement of activity observed at 3.12 µg/ml L-IND (0 to 1.5-log kill). However, in 10 mM SP buffer, some inhibition of activity at 12.5 µg/ml L-IND was observed with the addition of both pluronic and EDTA. Controls evaluating the effects of individual components showed that pluronic at either concentration in 10 mM SP reduced the activity of L-IND from 6-log kill to 1- to 1.5-log kill. EDTA had no effect. Additional experiments with L-IND and pluronic in SP buffer concentrations of 1, 2.5, and 5 mM were conducted. The effects of pluronic were most evident in those samples containing 0.5 wt % pluronic and SP at 5 mM with an approximately 4-log inhibition in kill. There was no effect in activity observed in the lower SP concentrations.

The effect of pluronic (0.25 and 0.5 wt %) on L-IND activity was also evaluated on *P. aeruginosa* in both 1 and 10 mM SP buffer. The effect of EDTA with L-IND on *P. aeruginosa* was not examined. *P. aeruginosa* was exposed for 4 hr at room temperature. Two concentrations of L-IND were evaluated, 32 µg/ml and 16 µg/ml, MIC and ½ MIC, respectively. The results indicate that pluronic at either concentration in 10 mM SP buffer with a 6-log kill, had no inhibitory effect on L-IND; however, interestingly, when formulated in the 1 mM SP buffer, a ~3-log inhibition in kill was observed at both concentrations of L-IND. At 16 µg/ml (½ MIC), some enhancement of activity was observed as compared to the controls without pluronic. The log kill was 2 to 3, but in the presence of pluronic at either concentration, the log kill was 6.

To confirm our findings, another matrix examining the effects of pluronic on L-IND (at 32 µ/ml for both *S. aureus* and *P. aeruginosa*) in 1 and 10 mM SP buffer was conducted. Again, the results on *S. aureus* show that when L-IND is combined with pluronic and 10 mM SP buffer a >3-log inhibition in kill is observed. With *P. aeruginosa*, the concentration of SP buffer does not appear to affect L-IND activity as greatly; however, higher activity is observed in 10 mM SP. The concentration of pluronic appears to inhibit L-IND activity somewhat with activity reduced by 1.5- to 3-logs in the presence of 0.5 wt % pluronic. No effect was observed at 0.25 wt % at either SP buffer concentration.

Example 12

On-Lens Performance (OLP) of L-IND as a Disinfecting Agent for Contact Lenses

In this experiment the disinfection of lenses using L-IND was evaluated.

Lenses were provided in borate buffered saline solution. The lenses were rinsed with sodium phosphate buffer before disinfection procedure. The lenses were transferred from buffer onto polypropylene pipette tips to dry at room temperature for ~5 min. The test organism was cultured and washed as described in the MIC protocol (Example 10).

The culture was resuspended in appropriate buffer at approximately $10^8$ CFU/ml. Then each side of the lens was innoculated with 10 µl of test organism by dropping 10 µl on the surface of aluminum foil, placing the lens on top convex side down, then dropping 10 µl on the concave side. The lens was allowed to sit 5 to 10 mins or to hang on a pipette tip to dry.

The nonabsorbed liquid from was wicked from the lens with sterile kimwipe and the lens was transferred to a 50 ml conical polypropylene tube containing ~10 ml L-IND at 50 µ/ml in buffer.

The lens was allowed to rehydrate, and then shaken vigorously (~30 sec). The lens was then maintained in the L-IND solution at room temperature ~4 hr.

After exposure, the tube was swirled or shaken to dislodge the lens from the tube surface and the lens was quickly transferred by pouring onto a vacuum filtration unit. The tube was rinsed with 40 to 50 ml 0.85% sodium chloride to neutralize the L-IND.

The filter and lenses were embedded in Mueller-Hinton agar and incubated at an appropriate temperature for 24 to 40 hrs for sufficient growth. Controls were prepared to determine inoculum density. The results are illustrated in Table 10.

TABLE 10

Results of on-lens study of indolicidin performance.

| Organism | MIC µg/ml | Log Kill in CFU |
| --- | --- | --- |
| *Pseudomonas aeruginosa* ATCC #9027 | 16 | >5 |
| *Staphylococcus aureus* ATCC #6538 | 16 | >5 |
| *Serratia marcescens* ATCC #13880 | 125 | >3 |
| *Candida albicans* ATCC #10231 | 64 | >4 |
| *Fusarium solani* ATCC #36031 | 64 | >4 |
| *Acanthamoeba divionensis* ATCC #50251* | 32 | >5 |
| *Acanthamoeba maritaniensis* ATCC #50253* | 32 | >5 |

*Not a required target organism in the FDA 510(k) Guidelines

Example 13

Long and Short Term Stability of Indolicidin

A) Short-term Stability Study of L-Indolicidin

Short term stability of indolicidin in a commercial container (RENU®, Bausch & Lomb) was evaluated. For this study L-indolicidin at 50 µg/ml in a 10 mM sodium phosphate buffer, pH 7.4, with and without 0.85% sodium chloride was measured against *S. aureus* ATCC 6538. Sampling time was at 0, 1, 2, 3, 7, 10 and 14 days and the exposure time of the test organism was 0.15 and 60 min, and 4 hours At each sampling point 2 aliquots were removed from each container. One sample was tested immediately for antimicrobial activity; the other sample was placed in a freezer. At the end of the 14 day study, all frozen samples were thawed and tested for antimicrobial activity on the same day.

Figure 2:
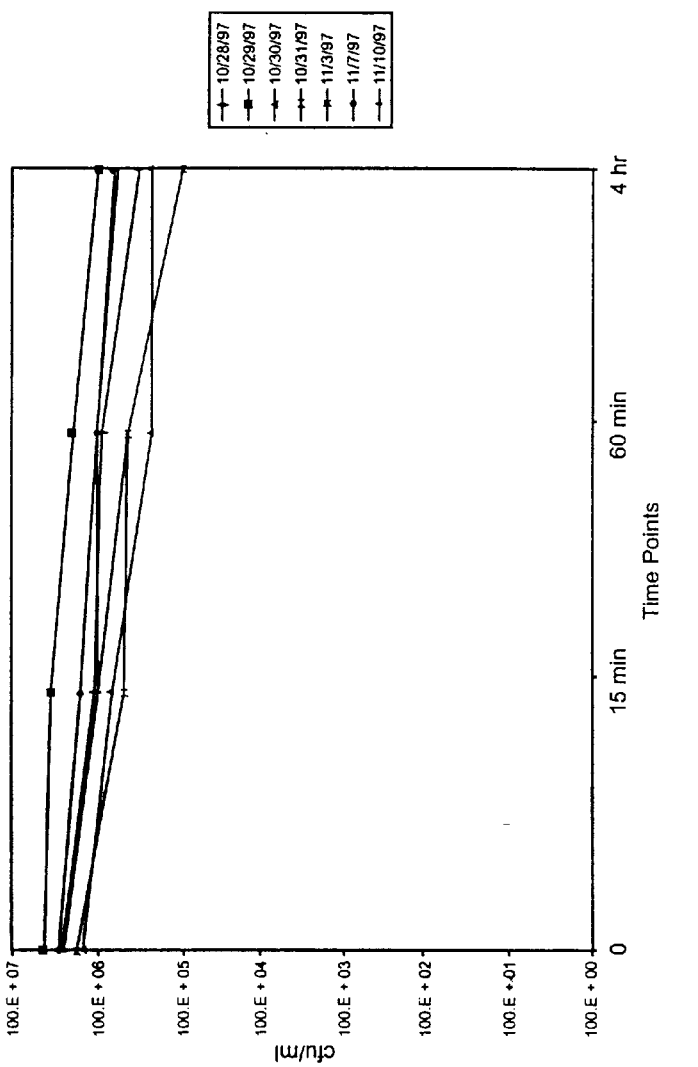
FIG. 2 illustrates the short term stability of unfrozen L-indolicidin in 10 mM sodium phosphate buffer with sodium chloride (note that although stable, absolute activity was low) as measured against S. aureus. The solution was stable exhibiting a dose dependent kill with only about a 1 log kill after a 4 hour exposure.
Figure 3:
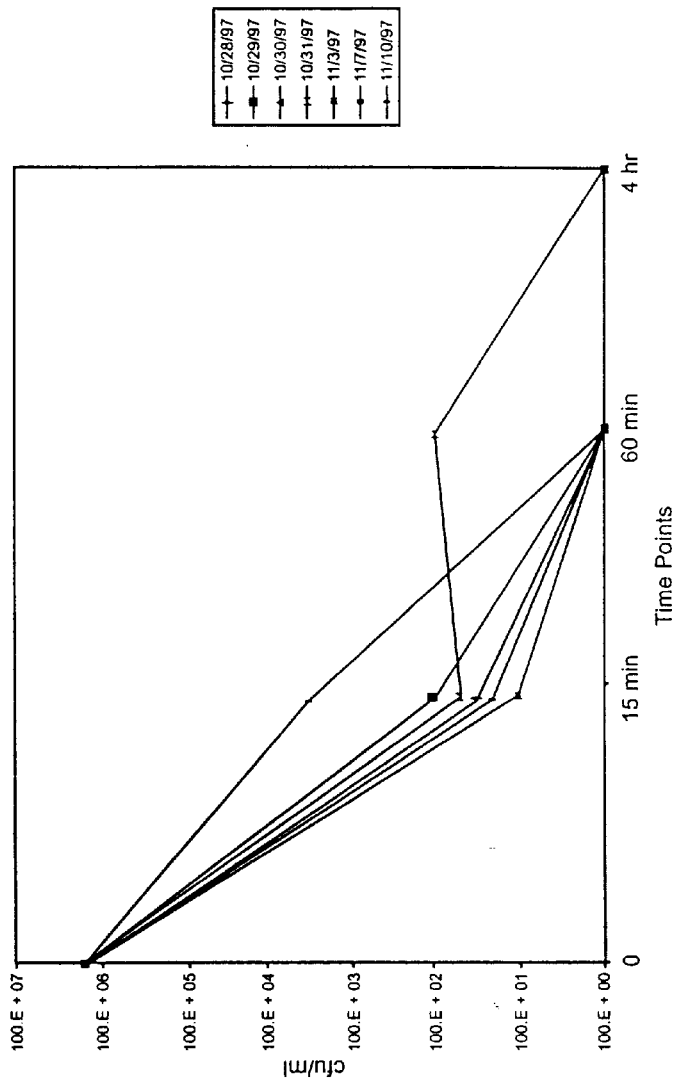
FIG. 3 illustrates the short term stability of frozen L-indolicidin in 10 mM sodium phosphate buffer as measured against S. aureus. The solution was stable exhibiting a time-dependent kill with a 6 log kill after a 60 minute exposure.
Figure 4:
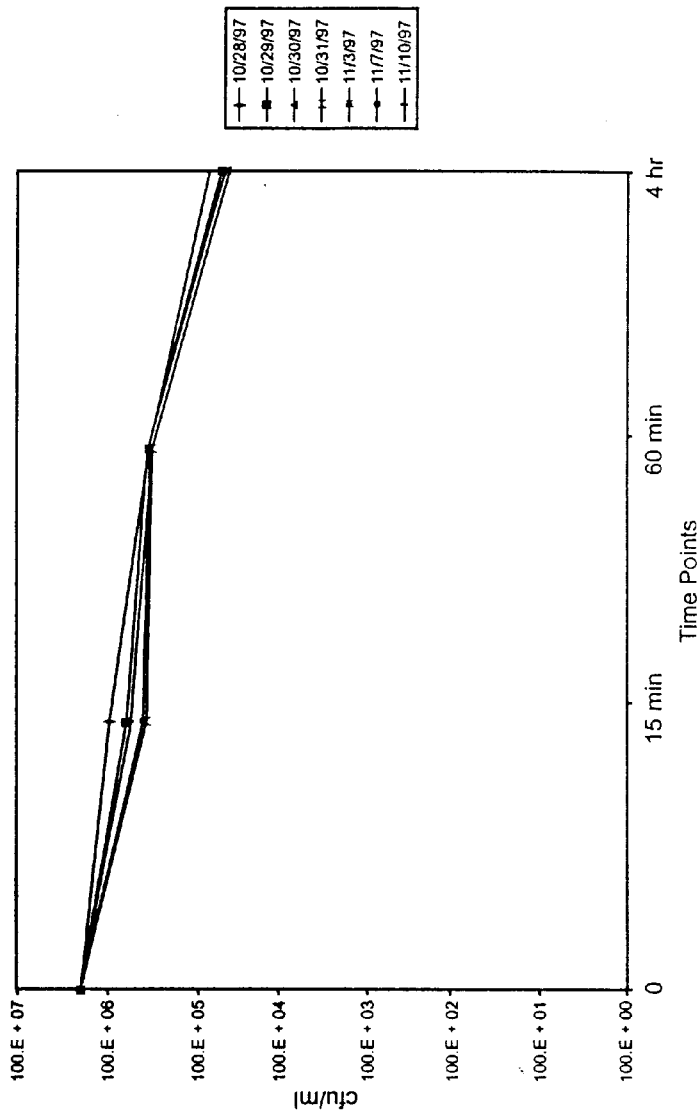
FIG. 4 illustrates the short term stability of frozen L-indolicidin in 10 mM sodium phosphate buffer as measured against S. aureus with sodium chloride. Frozen L-indolicidin was stable exhibiting a dose dependent kill with about 1.5 log kill after a 4 hour exposure.

Unfrozen L-indolicidin in 10 mM SP was stable exhibiting a time-dependent kill with a 4-log kill after a 4 hour exposure (FIG. 1). Unfrozen L-indolicidin in 10 mM SP with NaCl was stable exhibiting a dose dependent kill with only about a 1 log kill after a 4 hour exposure (FIG. 2). Frozen L-indolicidin in 10 mM SP was stable exhibiting a time-dependent kill with a 6 log kill after a 60 minute exposure (FIG. 3). Frozen L-indolicidin in 10 mM SP with NaCl was stable exhibiting a dose dependent kill with about 1.5 log kill after a 4 hour exposure (FIG. 4).

These data show that L-indolicidin is stable over a period of 14 days in 10 mM SP with and without 0.85% NaCl. However, the presence of NaCl reduces the antimicrobial activity of L-IND and the frozen samples exhibit higher antimicrobial activity compared to the samples that were tested immediately after removal from the commercial containers.

B) Long-term Stability Study of L-Indolicidin

Long term stability of indolicidin was evaluated in a commercial container (Rite-Aid). The L-indolicidin concentration was 50 μg/ml formulated in a 10 mM sodium phosphate buffer, pH 7.4, with and without 0.85% sodium chloride. The test organism was *S. aureus* ATCC 6538. Sampling time was 0, 1, 2, 3, 4 and 8 months. The exposure time of the test organism was 0 and 4 hours.

Figure 5:
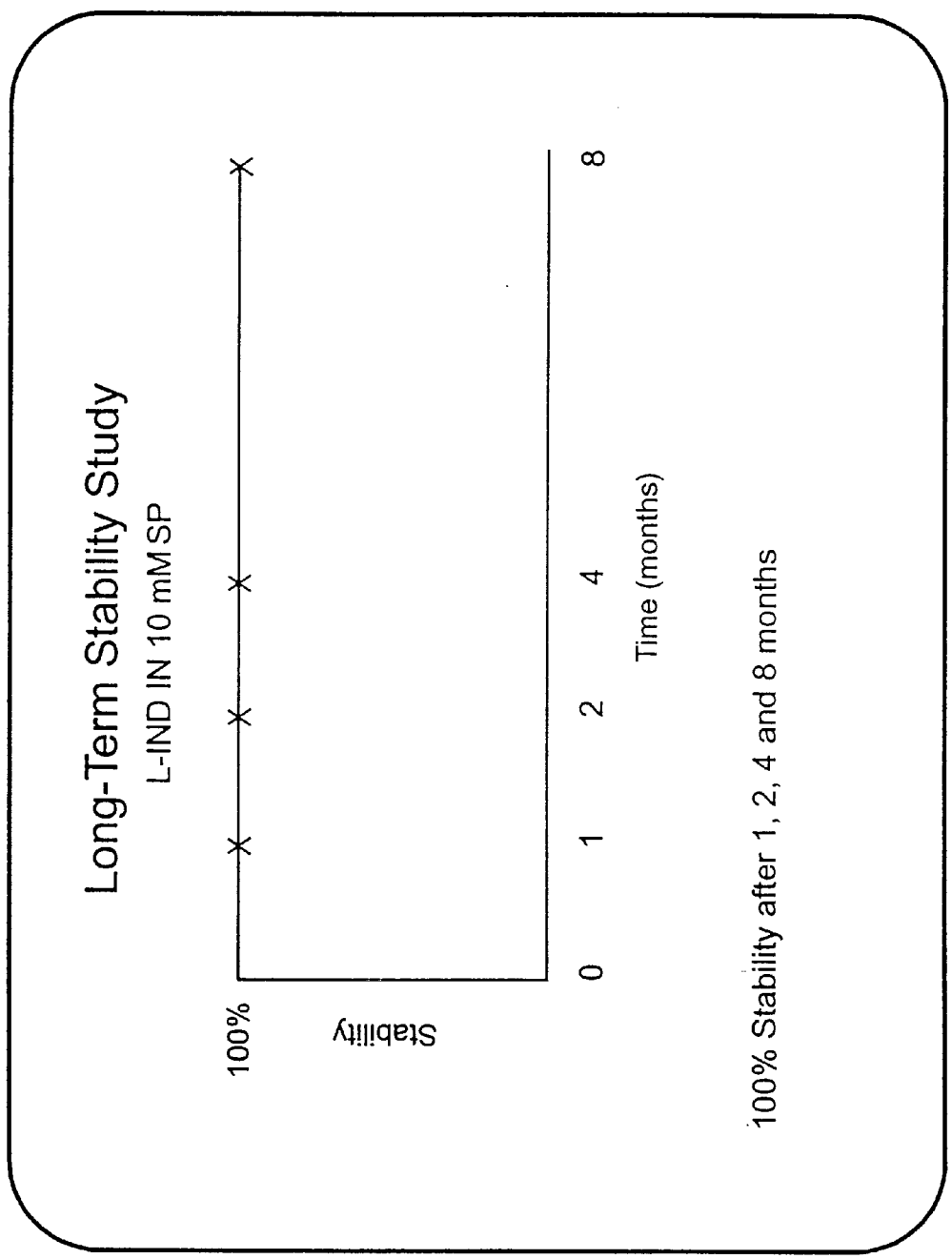
FIG. 5 illustrates the long term stability of unfrozen L-indolicidin in 10 mM sodium phosphate buffer as measured against S. aureus. The solution was stable over a period of 8 months exhibiting about a 4 log kill and thereby maintaining 100% stability.
Figure 6:
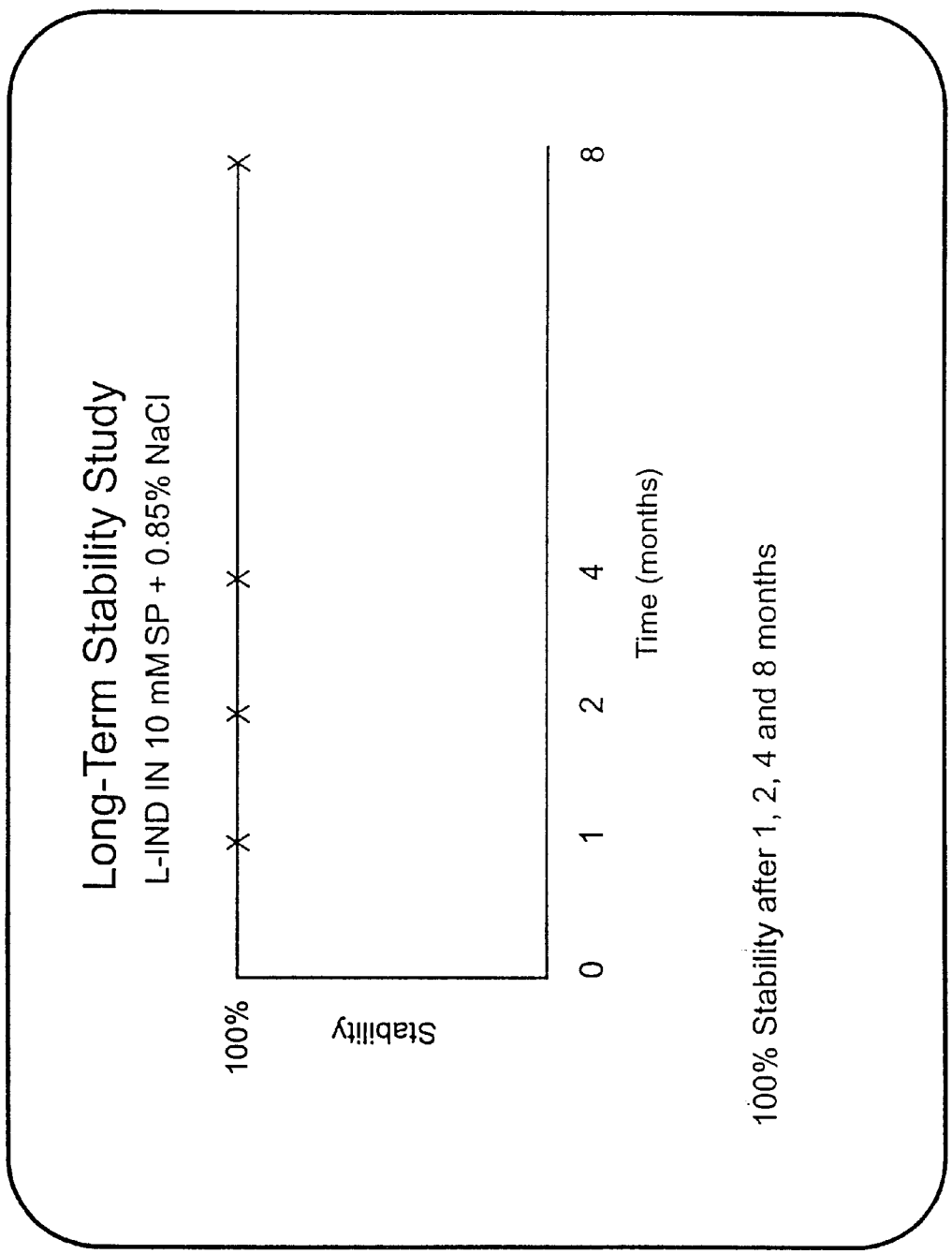
FIG. 6 illustrates the long term stability of unfrozen L-indolicidin in 10 mM sodium phosphate buffer with sodium chloride as measured against S. aureus. The solution was stable over a period of 8 months exhibiting about a 1 log kill, maintaining 100% stability.

L-indolicidin in 10 mM SP was stable over a period of 8 months exhibiting about a 4 log kill, maintaining 100% stability (FIG. 5). L-indolicidin in 10 mM SP with NaCl was stable over a period of 8 months exhibiting about a 1 log kill, but maintaining 100% stability (FIG. 6).

Example 14

Comparison of the Effect of Various Buffer Systems on Indolicidin Activity

In this experiment the effect of various buffer systems on the MIC of indolicidin (e.g., L-IND) was evaluated. The indolicidin was dissolved into one of 5 buffers: 1) sodium phosphate buffer, a mixture of $NaH_2PO_4$ and $Na_2HPO_4$ (SP); 2) HEPES: N-[2-hydroxyethyl]piperazine-2'-[2-ethanesulfonic acid]); 3) PIPES: piperazine-N,N'-bis[2-ethanesulfonic acid]; 4) TRIS: tris(hydroxymethyl)aminomethane; and 5) PBS: phosphate buffered saline.

The MIC determinations were performed in the various buffer systems as described in the MIC procedure (Example 9). The test organisms were *Staphylococcus aureus* (ATCC 6538) and *Pseudomonas aeruginosa* (ATCC 9027). The results of this study are summarized in Table 11.

TABLE 11

Results of study of buffer effect on indolicidin activity.

| Organism | Buffer conc nM | MIC (μg/ml) | | | |
|---|---|---|---|---|---|
| | | SP | HEPES | PIPES | TRIS |
| S. aureus | 1 | 8 | 8 | 8 | 8 |
| S. aureus | 5 | 16 | 8 | 8 | 8 |
| S. aureus | 10 | 32 | 8 | 16 | 8 |
| P. aeruginosa | 1 | 32 | >125 | >125 | 8 |
| P. aeruginosa | 5 | 16 | >125 | >125 | 8 |
| P. aeruginosa | 10 | 8 | >125 | >125 | 8 |

These data show that indolicidins in phosphate buffer maintain anti-microbicidal activity. These results are comparable to that found in hydrogen peroxide disinfection systems. See Example 1. Halide ion-free buffer systems are highly effective as are Good's buffers. It is noted that activity can vary as a function of buffer concentration. Thus, for example, SP and TRIS buffers show the broadest spectrum activity at concentrations of 1, 5, and 10 mM.

Example 15

Evaluation of Indolicidin Activity in Good's Buffers

In this experiment the effect of various components introduced into a Good's buffer (TRIS) on the MIC of indolicidin (e.g., L-IND) was evaluated. Because saline solution (e.g 0.85% NaCl) appears to reduce the antimicrobial activity of indolicidins in some buffers, NaCl was one of the additive evaluated. The indolicidin was dissolved into a TRIS buffer containing the additives as indicated in the tables below. The MIC determinations were performed in the various buffer systems as described in the MIC procedure (Example 9). The test organisms were as indicated below.

TABLE 12

Log kill of *S. aureus* exposed to 8 and 32 μg/ml L-indolicidin in three concentrations of Tris buffer without (Tris only), or with various additives.

| Additive (wt %) | 1 mM Tris | | 5 mM Tris | | 10 mM Tris | |
|---|---|---|---|---|---|---|
| | 8 μg/ml | 32 μg/ml | 8 μg/ml | 32 μg/ml | 8 μg/ml | 32 μg/ml |
| 0.85% NaCl | <1 | 1 | 1 | 6 | 1 | 6 |
| 0.2% EDTA | 6 | 6 | 6 | 6 | >3 | 6 |
| 0.5% Pluronic | 6 | 6 | 6 | 6 | 6 | 6 |
| Tris only | 6 | 6 | 6 | 6 | 6 | 6 |

TABLE 13

Log kill of *P. aeruginosa* exposed to 8 and 32 μg/ml L-indolicidin in three concentrations of Tris buffer without (Tris only), or with various additives.

| Additive (wt %) | 1 mM Tris | | 5 mM Tris | | 10 mM Tris | |
|---|---|---|---|---|---|---|
| | 8 μg/ml | 32 μg/ml | 8 μg/ml | 32 μg/ml | 8 μg/ml | 32 μg/ml |
| 0.85% NaCl | 1 | 1.5 | 1 | <1 | 0 | 0 |
| 0.2% EDTA | 5 | 5 | 5 | 5 | 5 | 5 |
| 0.5% Pluromc | 0 | 0 | 0 | 0 | 0 | 0 |
| Tris only | 0 | 0 | 0 | 0 | 4 | 4 |

TABLE 14

Log kill of *P. aeruginosa* exposed to 8 and 32 μg/ml L-indolicidin in three concentrations of Tris buffer without (Tris only), or with various additives (second test).

| Additive (wt %) | 1 mM Tris | | 5 mM Tris | | 10 mM Tris | |
|---|---|---|---|---|---|---|
| | 8 μg/ml | 32 μg/ml | 8 μg/ml | 32 μg/ml | 8 μg/ml | 32 μg/ml |
| 0.85% NaCl | 0 | 1 | 0 | 3 | NA | NA |
| 0.2% EDTA | 5 | 5 | 5 | 5 | 5 | 5 |
| 0.5% Pluronic | 0 | 0 | 0 | 0 | 0 | 0 |
| Tris only | 0 | 0 | 0 | 0 | 4 | 4 |

NA: Data not available, plating error.

Log kill of L-IND in SP at 5 mM was also conducted as a positive control. At 8 μg/ml there was a 1-log kill and at 32 μg/ml a 5-log kill was observed.

TABLE 15

Log kill of *E. coli* exposed to 8 and 32 μg/ml L-indolicidin in three concentrations of Tris buffer without (Tris only), or with various additives. (Second test)

| Additive (wt %) | 1 mM Tris | | 5 mM Tris | | 10 mM Tris | |
|---|---|---|---|---|---|---|
| | 8 μg/ml | 32 μg/ml | 8 μg/ml | 32 μg/ml | 8 μg/ml | 32 μg/ml |
| 0.85% NaCl | 0 | >3 | 0 | >2 | 0 | 2 |
| 0.2% EDTA | 5–6 | 5–6 | 5–6 | 5–6 | 5–6 | 6 |
| 0.5% Pluronic | 2 | >4 | 3 | 5–6 | NA | 5 |
| Tris only | 6 | 6 | 3 | 4 | 6 | 6 |

NA: Data not available, plating error.

Log kill of L-IND in SP at 5 mM was also conducted as a positive control. A 6-log kill was observed at both 8 and 32 μg/ml L-IND.

As illustrated in the foregoing tables, the addition of Pluronic to TRIS appears to eliminate the antimicrobial activity of the solution against *P. aeruginosa* while retaining antimicrobial activity against *S. aureus* and *E. coli*. The presence of EDTA results in high levels of activity against *S. aureus*, *P. aeruginosa,* and *E. coli* in all of the tests illustrated and EDTA even restores indolicidin activity against *P. aeurginosa* where the activity was lost in Tris only. For *S. aureus* and *E coli* at the concentrations tested, there was a direct correlation between peptide concentration and log kill, partially overcoming the deleterious effect of NaCl in low Goods' buffer concentrations.

It is understood that the examples and embodiments described herein are for illustrative purposes only and that various modifications or changes in light thereof will be suggested to persons skilled in the art and are to be included within the purview of this application and scope of the appended claims. All publications, patents, and patent applications cited herein are hereby incorporated by reference in their entirety for all purposes.

What is claimed is:

1. An ophthalmic composition for storing, cleaning, or disinfecting a contact lens, said composition comprising:
   an indolicidin in an antimicrobially effective amount; and
   a buffer compatible with application to a mammalian eye, wherein said buffer has a halide ion concentration less than 0.85 wt %, based on the total weight of the composition, and further, wherein the buffer comprises a boric acid, a borate salt, a poly(oxyethylene)-poly(oxypropylene) block copolymer, a chelating agent, a divalent cation, an antibacterial compound, an antifungal compound, an antiviral compound, an antimicrobial preservative other than indolicidin, a tonicity agent, or a surfactant.

2. The composition of claim 1, wherein said buffer comprises one or more salts selected from the group consisting of a phosphate, a carbonate, an acetate, a citrate, a borate, and a bicarbonate salt.

3. The composition of claim 2, wherein the salt is potassium or sodium.

4. The composition of claim 1, wherein the buffer comprises boric acid or a borate salt.

5. The composition of claim 4, wherein the boric acid or borate salt is in a microbistatic amount.

6. The composition of claim 2, wherein the pH of the composition is between 7.0 and 8.5.

7. The composition of claim 2, wherein the pH of the composition is between 7.2 and 7.5.

8. The composition of claim 1, wherein said composition is stable at 40° F. to 80° F. for at least 6 months.

9. The composition of claim 1, wherein the buffer comprises a poly(oxyethylene)-poly(oxypropylene) block copolymer.

10. The composition of claim 1, wherein the buffer comprises a chelating agent.

11. The composition of claim 10, wherein said chelating agent is selected from the group consisting of ethylenediaminetetraacetic acid (EDTA), ethylenediaminetetraacetic acid sodium salt, ethylenebis(oxyethylenenitrilo)tetraacetic acid (EGTA), and 2,2'-(ethylenediimino)-dibutyric acid (EDBA).

12. The composition of claim 1, wherein the buffer comprises a divalent cation.

13. The composition of claim 12, wherein the buffer comprises a divalent cation selected form the group consisting of $Ca^{+2}$, $Mg^{+2}$, $Zn^{+2}$, $Fe^{+2}$, and $Ba^{+2}$.

14. The composition of claim 1, wherein the buffer comprises an antibacterial, antifungal, or antiviral compound.

15. The composition of claim 1, wherein said indolicidin has an amino acid sequence selected from the group consisting of Ile-Leu-Pro-Trp-Lys-Trp-Pro-Trp-Trp-Pro-Trp-Arg-Arg-$NH_2$ (SEQ ID NO:1), Leu-Pro-Trp-Lys-Trp-Pro-Trp-Trp-Pro-Trp-Arg-Arg-$NH_2$, (SEQ ID NO:10), Pro-Trp-Lys-Trp-Pro-Trp-Trp-Pro-Trp-Arg-Arg-$NH_2$ (SEQ ID NO:11), Trp-Lys-Trp-Pro-Trp-Trp-Pro-Trp-Arg-Arg-$NH_2$ (SEQ ID NO:12), and Lys-Trp-Pro-Trp-Trp-Pro-Trp-Arg-Arg-$NH_2$ (SEQ ID NO:13).

16. The composition of claim 15, wherein said indolicidin has a carboxy-terminal homoserine or homoserine lactone.

17. The composition of claim 1, wherein the buffer comprises an antimicrobial preservative other than indolicidin.

18. The composition of claim 17, wherein said preservative is selected from the group consisting of benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, polyquad, potassium benzoate, potassium sorbate, propylparaben, propylparaben sodium, sodium benzoate, sodium dehydroacetate, sodium propionate, sorbic acid, sodium perborate, thimerosal, thymol, benzalkonium chloride, and chlorhexidine digluconate.

19. The composition of claim 17, wherein said preservative is a cecropin, a defensin, or a magainin.

20. The composition of claim 1, wherein the buffer comprises a tonicity agent selected from the group consisting of dextrose, glycerin, and mannitol.

21. The composition of claim 1 wherein the buffer comprises a surfactant.

22. The composition of claim 21 wherein said surfactant is selected from the group consisting of acacia, cholesterol, diethanolamine, glyceryl monostearate, lanolin, alcohols, lecithin, nonoglycerides, diglycerides, monoethanolamine, oleic acid, oleyl alcohol, poloxamer, polyoxyethylene 50 stearate, propylene glycol diacetate, propylene glycol monostearate, sodium lauryl sulfate, stearate, sorbitan monolaurate, sorbitan monooleate, sorbitan monopalmitate, sorbitan monostearate, stearic acid, and trolamine.

23. The composition of claim 14, wherein said antifungal compound is selected from the group consisting of amphotericin B, fluconazole, flucytosine, natamycin, miconazole nitrate, and ketoconazole.

24. The composition of claim 14, wherein said antibacterial compound is selected from the group consisting of bacitracin, chloramphenicol, ciprofloxacin hycrochloride, erythromycin, gentamycin sulfate, norfloxacin, olfloxacin, sulfacetamide sodium, tobramycin sulfate, olymyxin B, bacitracin zinc, neomycin, granicidin, oxytetracycline, trimethoprim, vancomycin hydrochloride, oxacillin, methicillin, imipenem, clindamycin, ceftazidime, amikacin, penicillin G, colistimethate sodium, cilastatin sodium, kanamycin sulfate, and ticarcillin disodium.

25. The composition of claim 1, wherein said indolicidin is present in a concentration of at least about 2 μg/ml.

26. The composition of claim 1, wherein said indolicidin is present in a concentration no greater than about 150 μg/ml.

27. The composition of claim 2, wherein said salt is present in a concentration of at least about 1 mM.

28. The composition of claim 2, wherein said salt is present in a concentration no greater than about 100 mM.

29. The composition of claim 2, wherein said salt is present in a concentration ranging from 1 mM to 10 mM.

30. The composition of claim 1, wherein said buffer comprises:
a sodium phosphate or potassium phosphate in a concentration ranging from about 1 mM to about 10 mM; and
a boric acid or borate salt in a concentration ranging from about 0. 1% to about 5%.

31. The composition of claim 1, wherein said buffer comprises:
a sodium phosphate or potassium phosphate salt in a concentration ranging from about 1 mM to about 10 mM; and
a poly(oxyethylene)-poly(oxypropylene) block copolymer in a concentration ranging from about 0.25 to about 0.5%.

32. The composition of claim 1, wherein said buffer comprises: a sodium phosphate or potassium phosphate in a concentration ranging from about 1 mM to about 10 mM; and
a divalent cation in a concentration ranging from about 5 mM to about 50 mM.

33. The composition of claim 1, wherein said buffer comprises:
a sodium phosphate or potassium phosphate in a concentration ranging from about 1 mM to about 10 mM; and
a chelator in a concentration ranging from about 0.01% and about 0.5%.

34. The composition of claim 10, wherein said poly (oxyethylene)-poly(oxypropylene) block copolymer is selected from the group consisting of poloxamer 182LF, poloxamer 188, poloxamer 331.

35. The composition of claim 1, wherein an effective concentration of said composition reduces the number of *Pseudomonas aeruginosa, Staphylococcus aureus,* and *Serratia marcescens* organisms by 3.0 logs or more within 4 hours.

36. The composition of claim 1, wherein an effective concentration of said composition reduces the number of *Candida albicans* and *Fusarium solani* by 1.0 log or more within 18 hrs.

37. The composition of claim 1, wherein said indolicidin is present in a concentration ranging from 2 μg/ml to 100 μg/ml and said buffer comprises:
a sodium phosphate or potassium phosphate in a concentration ranging from about 1 mM to about 10 mM;
a boric acid or borate salt in a concentration ranging from about 0. 1% to about 5%;
a poly(oxyethylene)-poly(oxypropylene) block copolymer in a concentration ranging from about 0.25 to about 0.5%;
a chelator in a concentration ranging from about 0.01% and about 0.5%; and
a divalent cation in a concentration ranging from about 5 mM to about 50 mM.

38. The composition of claim 1, comprising:
indolicidin having an amino acid sequence selected from the group consisting of Ile-Leu-Pro-Trp-Lys-Trp-Pro-Trp-Trp-Pro-Trp-Arg-Arg-NH$_2$ (SEQ ID NO:1), Leu-Pro-Trp-Lys-Trp-Pro-Trp-Trp-Pro-Trp-Arg-Arg-NH$_2$, (SEQ ID NO:10), Pro-Trp-Lys-Trp-Pro-Trp-Trp-Pro-Trp-Arg-Arg-NH$_2$ (SEQ ID NO:11), Trp-Lys-Trp-Pro-Trp-Trp-Pro-Trp-Arg-Arg-NH$_2$ (SEQ ID NO:12), and Lys-Trp-Pro-Trp-Trp-Pro-Trp-Arg-Arg-NH$_2$ (SEQ ID NO:13) where said indolicidin is present in a concentration ranging from about 5 μg/ml to about 125 μg/ml;
a sodium phosphate or potassium phosphate buffer in a concentration ranging from about 1 mM to about 10 mM at a pH ranging from about 7.2 to about 7.6; and
a poly(oxyethylene)-poly(oxypropylene) block copolymer present in a concentration ranging from about 0.25 wt % to about 0.5 wt %.

39. A method of disinfecting a contact lens, said method comprising contacting said contact lens with a composition of claim 1.

40. The method of claim 39, wherein the method reduces the number of *Pseudomonas aeruginosa, Staphylococcus aureus,* and *Serratia marcescens* organisms by 3.0 logs or more within 4 hours.

41. The method of claim 39, wherein the method reduces the number of *Candida albicans* and *Fusarium solani* by 1.0 log or more within 18 hours.

42. The method of claim 39, further comprising agitating said contact lens in said solution for at least about 5 seconds.

43. A contact lens storage system comprising a container containing a contact lens storage composition of claim 1.

44. The storage system of claim 43, wherein said container is composed of a compound selected from the group consisting of polycarbonate, polyethylene, polytetrafluorethylene (PTFE), polyvanillidinefluoride (PVF), and polypropylene.

45. The storage system of claim 43, wherein said solution is stable at 60° F. for at least 6 months.

46. The storage system of claim 43, wherein said container is a contact lens vial.

47. The storage system of claim 43, wherein said container is a contact lens case.

48. A method of packaging a contact lens, said method comprising sealing a contact lens in a container with an Ophthalmic composition of claim 1 wherein said contact lens in said container is not autoclaved.

49. A method of disinfecting a contact lens storage vessel, said method comprising contacting said storage vessel with a disinfecting solution comprising a composition of claim 1.

50. The method of claim 49, wherein said storage vessel is selected from the group consisting of a contact lens vial, a contact lens case, a contact lens shipping package.

51. The method of claim 49, further comprising agitating or mixing the solution in said storage vessel for at least about 5 seconds.

52. A multipurpose solution for care of a contact lens, said solution comprising:

an antimicrobial peptide that is an indolicidin and a buffer compatible with application to a mammalian eye, wherein the halide ion concentration of said buffer is less than 0.85 wt %; wherein said solution is suitable for two or more actions selected from the group consisting of contact lens disinfection, contact lens storage, contact lens cleaning, contact lens conditioning and rehydrating, contact lens moistening, and contact lens lubricating.

53. The multipurpose solution of claim 52, wherein said solution further comprises:

a poly(oxyethylene)-poly(oxypropylene) block copolymer; and a preservative other than an indolicidin.

54. The multipurpose solution of claim 53, wherein said preservative other than an indolicidin is selected from the group consisting of a benzalkonium chloride, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, polyquad, potassium benzoate, potassium sorbate, propylparaben, propylparaben sodium, sodium benzoate, sodium dehydroacetate, sodium propionate, sorbic acid, sodium perborate, thimerosal, thymol, benzalkonium chloride, and chlorhexidine digluconate.

55. The multipurpose solution of claim 53, wherein said preservative other than an indolicidin is selected from the group consisting of a crecropin, a defensin, and a magainin.

56. The multipurpose solution of claim 52, wherein said solution further comprises:

a demulcent.

57. The multipurpose solution of claim 56, wherein said solution further comprises a poly(oxyethylene)-poly(oxypropylene) block copolymer.

58. The multipurpose solution of claim 56, wherein said demulcent is selected from the group consisting of carboxymethylcellulose sodium, hydroxyethyl cellulose, hydroxypropyl methylcellulose, methylcellulose, dextran 70, gelatin, polyols, glycerin, polyethylene glycol 300, polyethylene glycol 400, polysorbate 80, propylene glycol, polyvinyl alcohol, polyvinyl pyrrolidone, polyethylene oxide, polystyrene sulfonate, polyacrylamide, polyethylene glycol 6000, and dextrose.

59. The multipurpose solution of claim 52, wherein said solution is stable at 60° F. for at least 6 months.

* * * * *